United States Patent
Matsuzaki et al.

(10) Patent No.: US 6,562,954 B1
(45) Date of Patent: May 13, 2003

(54) METHOD FOR PRODUCING OLIGOSACCHARIDE, AND NOVEL OLIGOSACCHARIDE AND PHARMACEUTICAL COMPOSITION CONTAINING THE SAME

(75) Inventors: Yuji Matsuzaki, Saitama (JP); Yousuke Yasuda, Saitama (JP); Satoshi Miyauchi, Tokyo (JP); Junichi Onaya, Tokyo (JP); Yusuke Hori, Tokyo (JP); Akira Tawada, Saitama (JP); Hideo Mochizuki, Tokyo (JP); Masami Iida, Kanagawa (JP)

(73) Assignee: Seikagaku Corporation, Tokyo (JP)

(*) Notice: Subject to any disclaimer, the term of this patent is extended or adjusted under 35 U.S.C. 154(b) by 0 days.

(21) Appl. No.: 09/478,025

(22) Filed: Jan. 5, 2000

(30) Foreign Application Priority Data

Jan. 7, 1999 (JP) ............................................. 11-002011

(51) Int. Cl.[7] ......................... C07H 17/02; A61K 31/70
(52) U.S. Cl. ..................... 536/17.2; 536/29.13; 536/53; 536/123.13; 514/25; 514/42
(58) Field of Search ................... 514/25, 42; 536/17.2, 536/29.13, 53, 123.13

(56) References Cited

U.S. PATENT DOCUMENTS

| | | | |
|---|---|---|---|
| 4,665,060 A | 5/1987 | Mårdh et al. | 514/61 |
| 4,851,338 A | 7/1989 | Mardh et al. | 435/34 |
| 5,489,578 A | 2/1996 | Rosen et al. | 514/61 |
| 5,514,660 A | 5/1996 | Zopf et al. | 514/25 |
| 5,580,862 A | 12/1996 | Rosen et al. | 514/61 |
| 5,939,403 A | 8/1999 | Maruyama et al. | 514/53 |

FOREIGN PATENT DOCUMENTS

| | | |
|---|---|---|
| EP | 0 361 490 | 4/1990 |
| EP | 0 795 560 A1 | 9/1997 |
| EP | 0 798 385 A2 | 10/1997 |
| EP | 0 926 154 A1 | 6/1999 |
| WO | WO 91/06303 | 5/1991 |
| WO | WO 93/24506 | 12/1993 |
| WO | WO 95/21618 | 8/1995 |

OTHER PUBLICATIONS

Craig Freeman, et al., Human liver N–acetylglucosamine–6–sulphate sulphatase, Biochem. J (1987) vol. 246, 355–365.

Gui–Hua Tai, et al., Human Corneal Keratan Sulfates, The Journal of Biological Chemistry, vol. 272, No. 45, Issue of Nov. 7 pp. 28227–28331, 1997.

N.M.Spijker, et al., Studies directed towards the synthesis of sulphated and non–sulphated glyco–conjugate fragments using insoluble silver–salt promoters, (1998), Recl. Trav. Chim. Pays—Bas 108, 360–368.

Rakesh K. Jain, et al., Synthesis of isomeric sulfated disaccharides. Methyl O–(2–acetamido–2–deoxy–3–O–, 4–O, and 6–O–sulfo–β–D–glucopyranosyl sodium salt)–(1→3)–β–D–galactopyranoside, Carbohydr. Res. (CRBRAT, 00086215); 1995: vol. 268 (2); pp. 279–285.

Masanori Kobayashi, et al., Synthetic Approach to Keratan Sulfate of Synthesis of Trsulfated Glycotetraose, Tetrahedron Letters vol. 30, No. 34, pp 4547–4550, 1989.

Shin Yazawa, et al. Abstracts of XXth Japanese Carbohydrate symposium, Jul. 15–17, 1998, Sapporo, Japan, p. 93, translation of Summary only.

*Primary Examiner*—Kathleen K. Fonda
(74) *Attorney, Agent, or Firm*—Knobbe, Martens, Olson & Bear, LLP

(57) ABSTRACT

Oligosaccharides including those usable as anti-inflammatory agent or anti-allergy agent, represented by the following general formula (3):

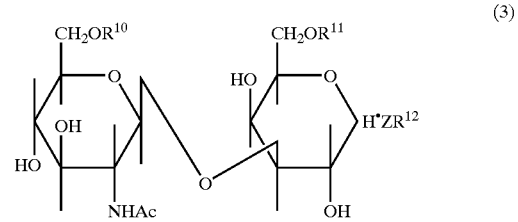

(3)

wherein $R^{10}$ and $R^{11}$ each independently represent a hydrogen atom or —$SO_3M$ where M represents a proton or a monovalent cation, Ac represents an acetyl group, $R^{12}$ represents a hydrogen atom or an anomeric substituent (a 6-O-sulfated N-acetylglucosamine residue, an alkyl group, a glycerol residue, an O-alkylglycerol residue, a cholesterol residue, a cholestanyl group, a ceramide residue, a phospholipid residue, a biotin residue, or a peptide residue), and Z represents an oxygen atom or —NHCO—.

6 Claims, 12 Drawing Sheets

L4

L4L4

K4

K2

G4L4

*p<0.05, **p<0.01 v.s. control

METHOD FOR PRODUCING OLIGOSACCHARIDE, AND NOVEL OLIGOSACCHARIDE AND PHARMACEUTICAL COMPOSITION CONTAINING THE SAME

BACKGOUND OF THE INVENTION

The present invention relates to a method for producing an oligosaccharide. The present invention also relates to a novel oligosaccharide and a pharmaceutical composition containing it.

Keratan sulfate is a glycosaminoglycan comprising, as a basic structure, N-acetyl lactosamine in which the 6-position of the N-acetyl glucosamine residue is O-sulfated. It has been reported that some of degradation products of karatan sulfate, i.e., keratan sulfate oligosaccharides, have a pharmacological activity (see, for example, International Publication No. WO96/16973).

As a disaccharide structure derived from keratan sulfate, those shown in FIG. 1 may be expected. However, searching of another keratan sulfate oligosaccharide having a pharmacological activity has been limited, because it has been difficult to obtain a keratan sulfate oligosaccharide as a disaccharide having a galactose residue at its reducing end (GlcNAcβ1→3Gal where Gal represents galactose, GlcN represents glucosamine, and Ac represents an acetyl group) and having a sulfate group like keratan sulfate. For example, even by treating keratan sulfate with known endo-β-galactosidases, it is difficult to obtain a disaccharide having a galactose residue at its reducing end (GlcNAcβ1→3Gal) with a sulfate group retained.

SUMMARY OF THE INVENTION

A first object of the present invention is to provide a method that makes it possible to easily produce a keratan sulfate disaccharide having a galactose residue at its reducing end.

A second object of the present invention is to provide a novel oligosaccharide having a pharmacological activity, and to provide it as a medicine.

The inventors of the present invention found that a disaccharide having a galactose residue at its reducing end could be obtained through glycosidic linkage formation by protecting hydroxyl groups and an amino group in glucosamine, and hydroxyl groups in galactose in a particular manner. Moreover, they also found that disaccharides in which hydroxyl groups at particular positions were sulfated had excellent pharmacological activities. The present invention has been accomplished based on these findings.

The present invention provides a method for producing an oligolsaccharide represented by the following general formula (3):

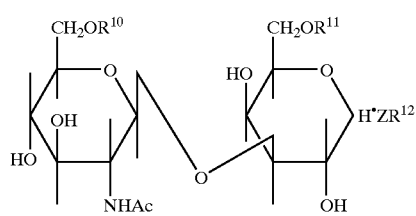

wherein $R^{10}$ and $R^{11}$ each independently represent a hydrogen atom or —$SO_3M$ where M represents a proton or a monovalent cation, Ac represents an acetyl group, $R^{12}$ represents a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, and Z represents an oxygen atom or —NHCO—, which method comprises at least a step of carrying out glycosidic linkage formation between a monosaccharide represented by the following general formula (1):

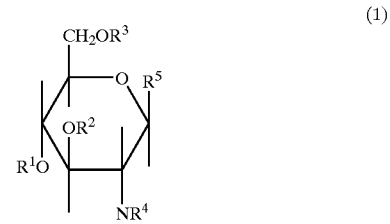

wherein $R^1$ and $R^2$ each independently represent an aralkyl group, $R^3$ represents an acyl group or a silyl group, $R^4$ represents a protective group for an amino group, and $R^5$ represents a leaving group, and a monosaccharide represented by the following general formula (2):

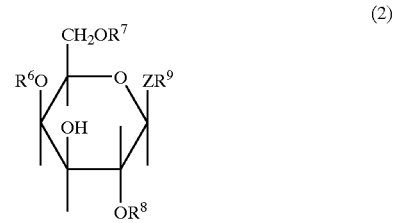

wherein $R^6$ and $R^8$ each independently represent an aralkyl group, $R^7$ represents an acyl group or a silyl group, $R^9$ represents an aralkyl group, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, and Z represents an oxygen atom or —NHCO— (this method is also referred to as the "production method of the present invention" hereinafter).

In the production method of the present invention, it is preferred that at least one of $R^{10}$ and $R^{11}$ represents —$SO_3M$ where M represents a proton or a monovalent cation, and the method comprises, after the step of carrying out the glycosidic linkage formation between the monosaccharide represented by the aforementioned general formula (1) and the monosaccharide represented by the aforementioned general formula (2), a step of substituting a hydrogen atom for at least one of $R^3$ and $R^7$, and subsequently substituting —$SO_3M$ for the hydrogen atom.

In a preferred embodiment of the production method of the present invention, the aforementioned general formulae (1)–(3) are represented by the following formulae (4)–(6), respectively:

(4)

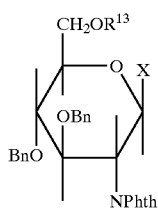

wherein Bn represents a benzyl group, $R^{13}$ represents an acetyl group or a levulinoyl group, and Phth represents a phthaloyl group, and X represents a halogen atom;

(5)

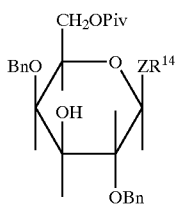

wherein Bn represents a benzyl group, $R^{14}$ represents a benzyl group, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, Z represents an oxygen atom or —NHCO—, and Piv represents a pivaloyl group; and (6)

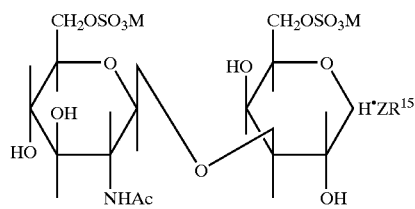

wherein, Ac represents acetyl group, and M represents a proton or a monovalent cation, $R^{15}$ represents a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, and Z represents an oxygen atom or —NHCO—.

In another preferred embodiment of the production method of the present invention, the aforementioned general formulae (1)–(3) are represented by the following formulae (7)–(9), respectively:

(7)

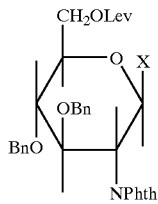

wherein, Bn represents a benzyl group, Lev represents a levulinoyl group, and Phth represents a phthaloyl group, and X represents a halogen atom;

(8)

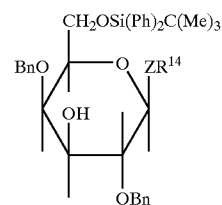

wherein, Bn, $R^{14}$ and Z are as defined above, Ph represents a phenyl group, and Me represents a methyl group; and (9)

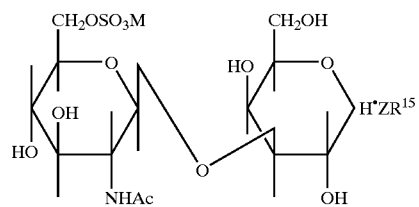

wherein, $R^{15}$ and Z are as defined above, Ac represents an acetyl group, and M represents a proton or a monovalent cation.

In a further preferred embodiment of the production method of the present invention, the aforementioned general formulae (1)–(3) are represented by the following formulae (10)–(12), respectively:

(10)

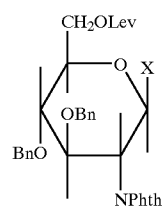

wherein, Bn represents a benzyl group, Lev represents a levulinoyl group, and Phth represents a phthaloyl group, and X represents a halogen atom;

(11)

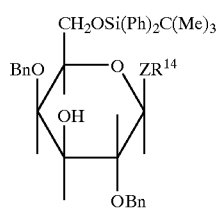

wherein, Bn, $R^{14}$ and Z are as defined above, Ph represents a phenyl group, and Me represents a methyl group; and

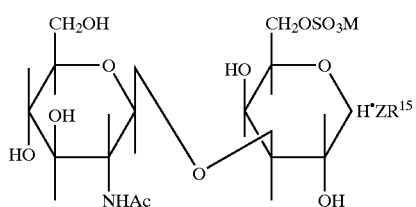

(12)

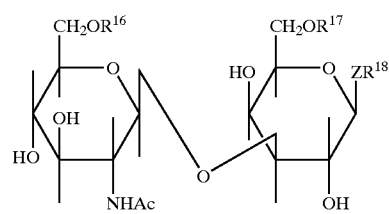

(13)

wherein, $R^{15}$ and Z are as defined above, Ac represents an acetyl group, and M represents a proton or a monovalent cation.

The present invention also provides an oligosaccharide represented by the following general formula (13):

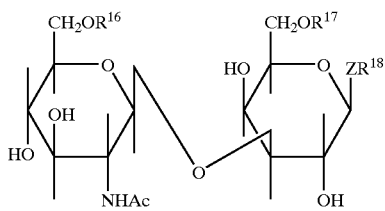

(13)

wherein, $R^{16}$ and $R^{17}$ each independently represent a hydrogen atom or —$SO_3M$ where M represents a proton or a monovalent cation, Ac represents an acetyl group, $R^{18}$ represents a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, and Z represents an oxygen atom or —NHCO—, provided that an oligosaccharide wherein both of $R^{16}$ and $R^{17}$ are hydrogen atoms, Z is an oxygen atom and $R^{18}$ is a hydrogen atom or a cholestanyl group, and an oligosaccharide wherein $R^{16}$ represents —$SO_3M$ where M represents a proton or a monovalent cation, Z is an oxygen atom and both of $R^{17}$ and $R^{18}$ are hydrogen atoms are excluded (The oligosaccharide is also referred to as the "oligosaccharide of the present invention" hereinafter).

In a preferred embodiment of the oligosaccharide of the present invention, each of $R^{16}$ and $R^{17}$ is —$SO_3M$ where M represents a proton or a monovalent cation.

In another preferred embodiment of the oligosaccharide of the present invention, $R^{16}$ is a hydrogen atom, and $R^{17}$ is —$SO_3M$ where M represents a proton or a monovalent cation.

In the oligosaccharide of the present invention, $R^{18}$ is preferably a hydrogen atom, a 6-O-sulfated N-acetylglucosamine residue, an alkyl group, an O-alkylglycerol residue or a cholestanyl group, and Z is an oxygen atom.

The present invention further provides a medicine comprising, as an active ingredient, the oligosaccharide of the present invention represented by the following general formula (13):

wherein, $R^{16}$ and $R^{17}$ each independently represent a hydrogen atom or —$SO_3M$ where M represents a proton or a monovalent cation, Ac represents an acetyl group, $R^{18}$ represents a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, and Z represents an oxygen atom or —NHCO—, provided that an oligosaccharide wherein both of $R^{16}$ and $R^{17}$ are hydrogen atoms, Z is an oxygen atom and $R^{18}$ is a hydrogen atom or a cholestanyl group is excluded, or a pharmaceutically acceptable salt thereof (The medicine is also referred to as the "medicine of the present invention" hereinafter).

In particular, the oligosaccharide of the present invention wherein $R^{16}$ is —$SO_3M$, and $R^{17}$ is a hydrogen atom or —$SO_3M$ where M represents a proton or a monovalent cation, or a pharmaceutically acceptable salt thereof is useful as an anti-allergy agent, and the oligosaccharide of the present invention wherein both of $R^{16}$ and $R^{17}$ are —$SO_3M$ where M represents a proton or a monovalent cation, or a pharmaceutically acceptable salt thereof is useful as an anti-inflammatory agent.

The present invention also provides a pharmaceutical composition comprising the oligosaccharide of the present invention usable for the medicine and a pharmaceutically acceptable carrier. In particular, an anti-allergy composition comprising the oligosaccharide of the present invention usable for the anti-allergy agent and a pharmaceutically acceptable carrier, and an anti-inflammatory composition comprising the oligosaccharide of the present invention usable for the anti-inflammatory agent and a pharmaceutically acceptable carrier are provided. In addition, the present invention provides a method for preventing or treating allergy, which comprises administering a therapeutically effective amount of the oligosaccharide of the present invention usable for the anti-allergy agent to a subject in need of such treatment, and a method for preventing or treating inflammation, which comprises administering a therapeutically effective amount of the oligosaccharide of the present invention usable for the anti-inflammatory agent to a subject in need of such treatment.

DETAILED DESCRIPTION OF THE INVENTION

Figure 1:
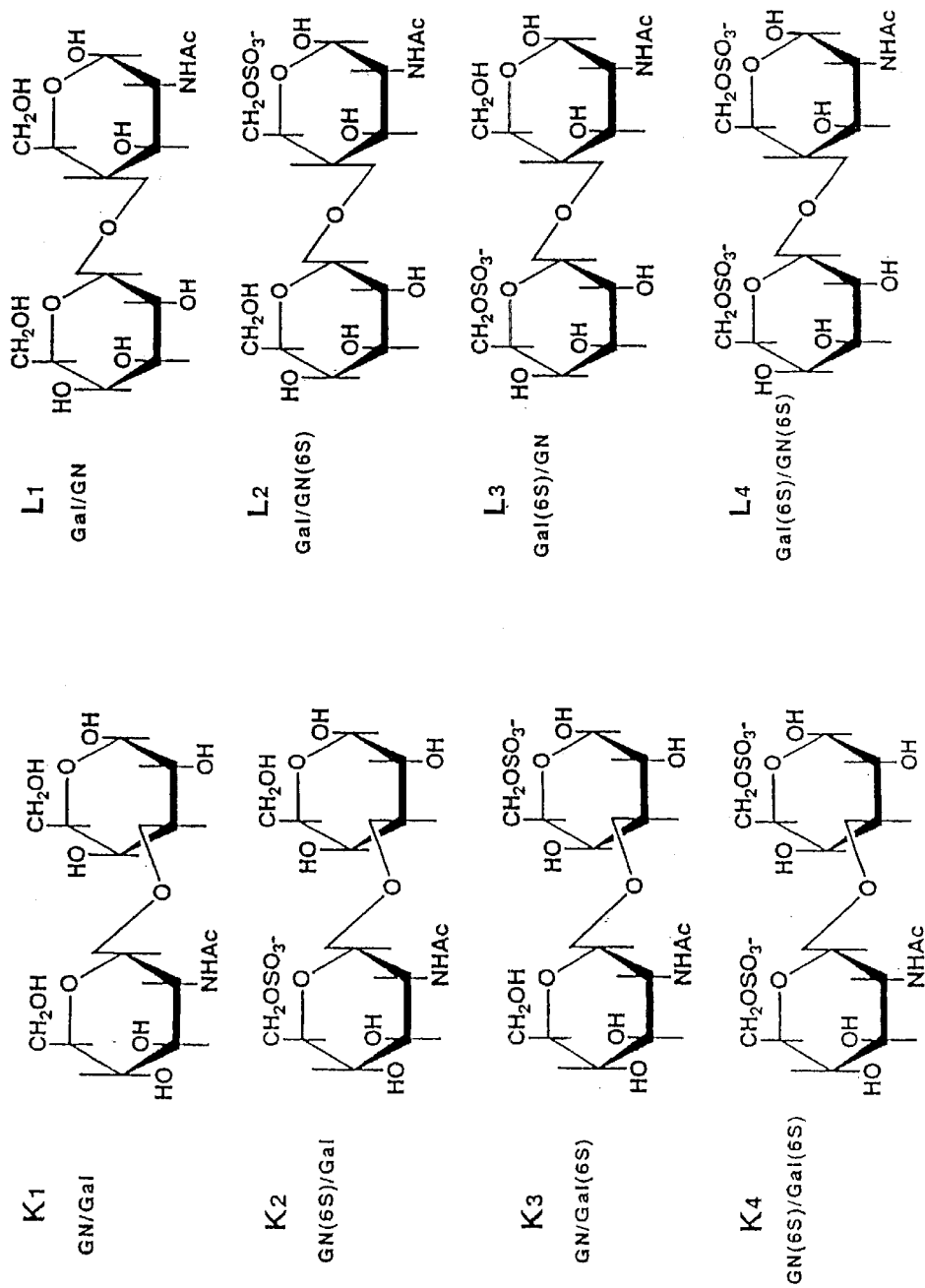
FIG. 1 shows structures of keratan sulfate disaccharides expected from the structure of keratan sulfate.

Embodiments of the present invention will be explained blow.

Abbreviations commonly used in the present specification and the appended drawings are listed first together with the meanings thereof, which are indicated in parentheses following each abbreviation.

Ac (acetyl group)
Bn (benzyl group)
Phth (phthaloyl group)
Piv (pivaloyl group)
Lev (levulinoyl group)
Ph (phenyl group)
Me (methyl group)
All (allyl group)
MP (p-methoxyphenyl group)
M (proton or monovalent cation)
X (halogen atom)

<1> Production Method of the Present Invention

The production method of the present invention is a method for producing the oligosaccharide represented by the general formula (3), and comprises at least the step of carrying out glycosidic linkage formation between the monosaccharide represented by the general formula (1), and the monosaccharide represented by the general formula (2).

The substituents in the compounds of the general formulae (1)–(3) are as follows.

$R^1$, $R^2$, $R^6$ and $R^8$ each independently represent an aralkyl group. Examples of the aralkyl group include benzyl, p-methoxybenzyl, phenethyl, 3-phenylpropyl, p-nitrobenzyl, o-nitrobenzyl, p-halobenzyl, p-cyanobenzyl, diphenylmethyl, triphenylmethyl (trityl), α- or β-naphthylmethyl, and α-naphthyldiphenylmethyl groups. $R^1$, $R^2$, $R^6$ and $R^8$ each preferably represent a benzyl group.

$R^3$ and $R^7$ each independently represent an acyl group or a silyl group. Examples of the acyl group include acetyl, pivaloyl, levulinoyl, benzoyl, chloroacetyl, dichloroacetyl, trifluoroacetyl, methoxyacetyl, propionyl, n-butyryl, (E)-2-methylbutenoyl, isobutyryl, pentanoyl, o-(dibromomethyl)benzoyl, o-(methoxycarbonyl)benzoyl, p-phenylbenzoyl, 2,4,6-trimethylbenzoyl, p-toluoyl, p-anisoyl, p-chlorobenzoyl, p-nitrobenzoyl, and α-naphthoyl groups. Examples of the silyl group include trimethylsilyl, triethylsilyl, dimethylisopropylsilyl, isopropyldimethylsilyl, methyl(di-t-butyl)silyl, t-butyldimethylsilyl, t-butyldiphenylsilyl, triisopropylsilyl, and tetraisopropyldisiloxanyl groups.

It is preferred that $R^3$ and $R^7$ each independently represent an acyl group, or $R^3$ represents an acyl group and $R^7$ represents a silyl group. Preferred examples of the acyl group are an acetyl group, a pivaloyl group, and a levulinoyl group, and a preferred example of the silyl group is a t-butyldiphenylsilyl group.

$R^4$ represents a protective group for an amino group, and examples of the protective group include phthaloyl, acetyl, and allyloxycarbonyl groups. It is preferably a phthaloyl group.

$R^5$ represents a leaving group. The term "leaving group" used herein means a group leaving under a condition in which the glycosidic linkage formation between the monosaccharide represented by the general formula (1), and the monosaccharide represented by the general formula (2) is performed. Examples of the leaving group include halogen atoms (fluorine atom, chlorine atom, bromine atom etc.), an imido group, a methylthio group, and a phenylthio group. It is preferably a halogen atom, particularly preferably a fluorine atom.

X in the formulae (4), (7) and (10) is preferably a halogen atom among the leaving groups. X is particularly preferably a fluorine atom as mentioned above.

$R^9$ represents an aralkyl group, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue. The residue used herein means a remaining moiety in which an atom or a atom group involving in bonding of a compound is removed from the compound.

Examples and preferable ones of the aralkyl group are as described above.

The 6-O-sulfated N-acetylglucosamine residue is usually a residue in which a hydroxyl group at 4-position is removed.

The alkyl group is exemplified by those having carbon number of 1 to 23, preferably 8 to 14.

The glycerol residue is usually a residue in which one of hydroxyl groups is removed.

The O-alkylglycerol residue is not limited specifically, but usually a residue in which one of hydroxyl groups is removed. It is preferably a di-O-alkylglycerol residue, more preferably 2,3-di-O-alkylglycerol residue. The "alkyl" used herein is exemplified by those having carbon number of 1 to 23, preferably 8 to 14.

The O-acylglycerol residue is not limited specifically, but usually a residue in which one of hydroxyl groups is removed. It is preferably a di-O-acylglycerol residue, more preferably 2,3-di-O-acylglycerol residue. The "acyl" used herein is exemplified by those having carbon number of 1 to 23, preferably 8 to 14.

The cholesterol residue is usually a residue in which a hydroxyl group at C-3 of a cyclopentaphenanthrene ring is removed.

The ceramide residue is usually a residue in which a hydroxyl group at 1-position is removed. The N-acyl group in the ceramide usually has carbon number of 1 to 28, preferably 14 to 23.

Examples of the phospholipid residue include glycerophospholipid (phosphatidylcholine, phosphatidylethanolamine, phosphatidylserine, phosphatidylinositol, etc.) residues and sphingophospholipid (sphingomyelin, etc.) residues.

The biotin residue is usually a residue in which a carboxyl group is removed.

The peptide residue is usually any one of amino and carboxyl groups is removed.

Z represents an oxygen atom or —NHCO—. Any of the nitrogen atom and the oxygen atom in —NHCO— may be on the $R^9$ side.

When $R^9$ is an aralkyl group, a 6-O-sulfated N-acetylglucosamine residue, an alkyl group, a glycerol residue, an O-alkylglycerol residue, an O-acylglycerol residue, a cholesterol residue, a cholestanyl group, a ceramide residue or a phospholipid residue, Z is preferably an oxygen atom.

When $R^9$ is a biotin residue or a peptide residue, Z is preferably —NHCO—.

$R^{10}$ and $R^{11}$ each independently represent a hydrogen atom or —$SO_3M$.

$R^{12}$ represents a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue. These groups and residues are as described with respect to $R^9$.

When $R^{12}$ is a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue or a phospholipid residue, Z is preferably an oxygen atom.

When $R^{12}$ is a biotin residue or a peptide residue, Z is preferably —NHCO—.

The condition for the glycosidic linkage formation may be suitably selected depending on the leaving group to be used. For example, when a fluorine atom is selected as the leaving group, a condition of a reaction time of 5 minutes to 50 hours and a reaction temperature of −70 to 60° C. may be used. The solvent is not particularly limited, and 1,2-dichloroethane and so forth can be used.

The aralkyl group, the acyl group or the silyl group, and the protective group for the amino group are selected so that they should not be released under the condition in which the leaving group is released. These groups may be the same groups.

Figure 2:
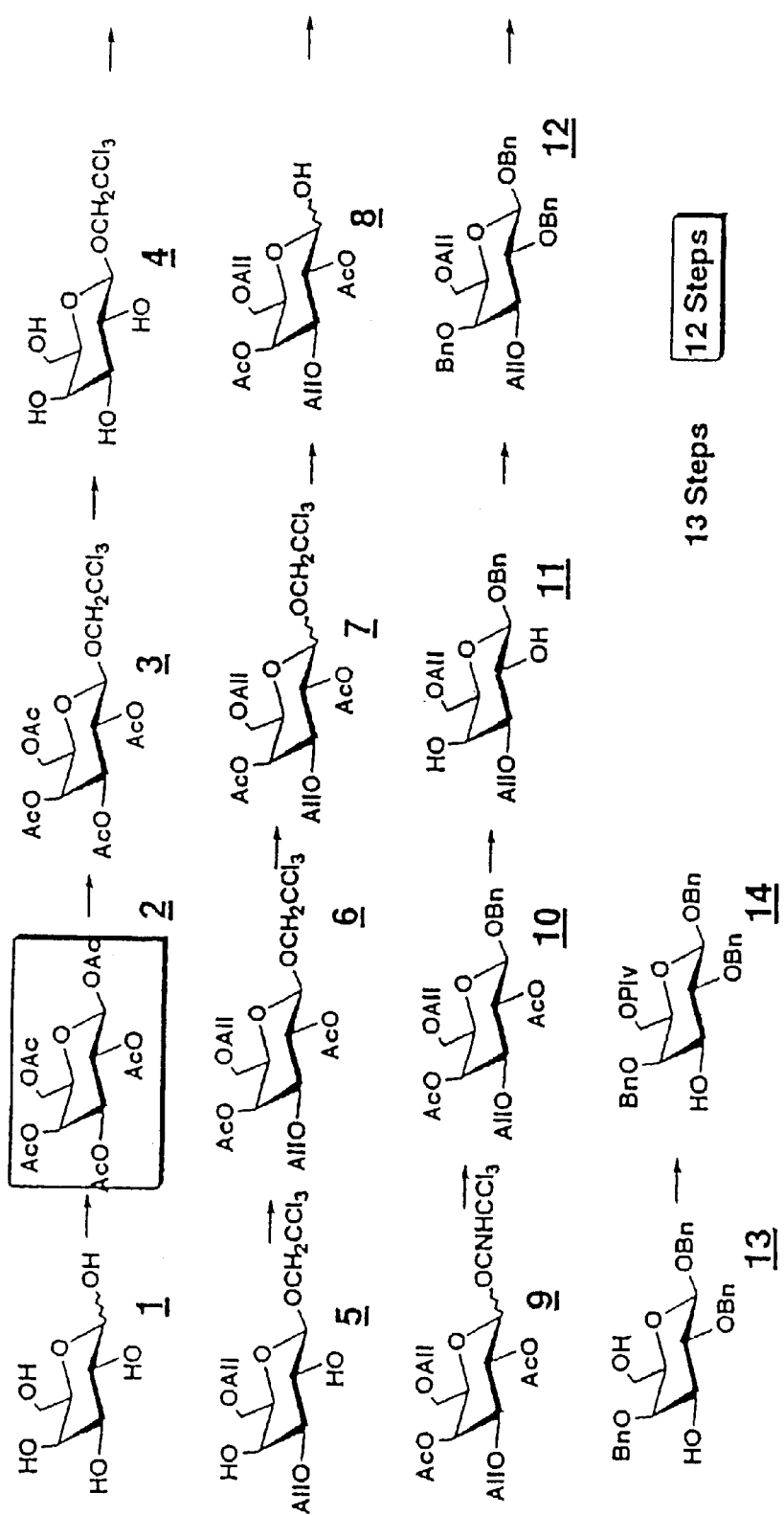
FIG. 2 outlines an example of a method for producing a starting material for the production of the oligosaccharide of the present invention.

The monosaccharide of the general formula (2) can be produced by, for example, the method outlined in FIG. 2. That is, the syntheses from Compound 2 to Compound 9 can be performed starting from galactose (Compound 1) according to the synthetic route reported by Ito et al. (Agric. Biol. Chem., 50, 3227 (1986)). The syntheses of Compound 10 to Compound 14 can be performed according to a synthetic route comprising substitution of a benzyl group for a trichloroacetoimido group (Compound 10), deacetylation (Compound 11), benzylation (Compound 12), deallylation (Compound 13), and pivaloylation (Compound 14). Conditions for these steps may be suitably selected by those skilled in the art.

Figure 3:
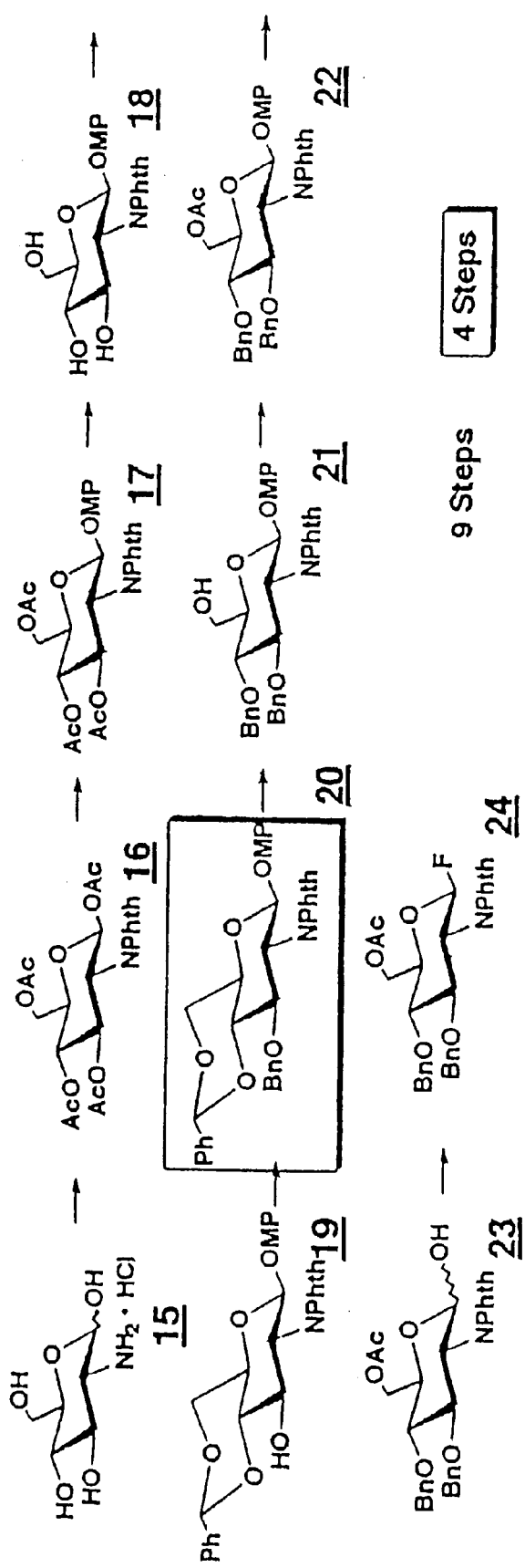
FIG. 3 also outlines an example of a method for producing a starting material for the production of the oligosaccharide of the present invention.

The monosaccharide of the general formula (1) can be produced by, for example, the method outlined in FIG. 3. That is, the syntheses of Compound 16 to Compound 20 can be performed starting from glucosamine (Compound 15) according to the synthetic route reported by Nakano et al. (Tetrahedron Lett., 31, 1597 (1990)). The syntheses of Compound 21 to Compound 24 can be performed according to the synthetic route comprising decyclization of the benzylidene group between the 4- and 6-positions (Compound 21), acetylation (Compound 22), demethoxyphenylation (Compound 23) and fluorination (Compound 24). Conditions for these steps may be suitably selected by those skilled in the art.

After carrying out the glycosidic linkage formation between the monosaccharide of the general formula (1), and the monsaccharide of the general formula (2), the oligosaccharide of the general formula (3) can be obtained by eliminating the aralkyl group, and the acyl group or the silyl group, and substituting the acetyl group for the protective group for the amino group. The glycosidic linkage formation, and elimination and substitution of such groups as mentioned above can be performed by known methods (for example, Synthesis, 384, (1989)). Specific examples of these reactions will be described in the examples mentioned below.

When at least one of $R^{10}$ and $R^{11}$ in the general formula (3) represents —$SO_3M$, after the glycosidic linkage formation between the monosaccharide represented by the general formula (1) and the monosaccharide represented by the general formula (2), selective elimination of at least one of $R^3$ and $R^7$ (an acyl group or a silyl group) to substitute a hydrogen atom for it (thereby a hydroxyl group is formed), and substitution of —$SO_3M$ for the hydrogen atom (sulfation) may be performed.

The selective elimination (and the substitution of the hydrogen atom) of the acyl group or the silyl group can be performed by suitably selecting an acyl group or a silyl group as for the aralkyl group and the protective group for the amino group. Examples of such a combination include a combination of a benzyl group as the aralkyl group, a phthaloyl group as the protective group for the amino group, and an acetyl group or a pivaloyl group as the acyl group or the silyl group. The method for the sulfation is also not particularly limited, and any known methods may be used. Specific examples of these reactions will be described in the examples mentioned below.

Figure 4:
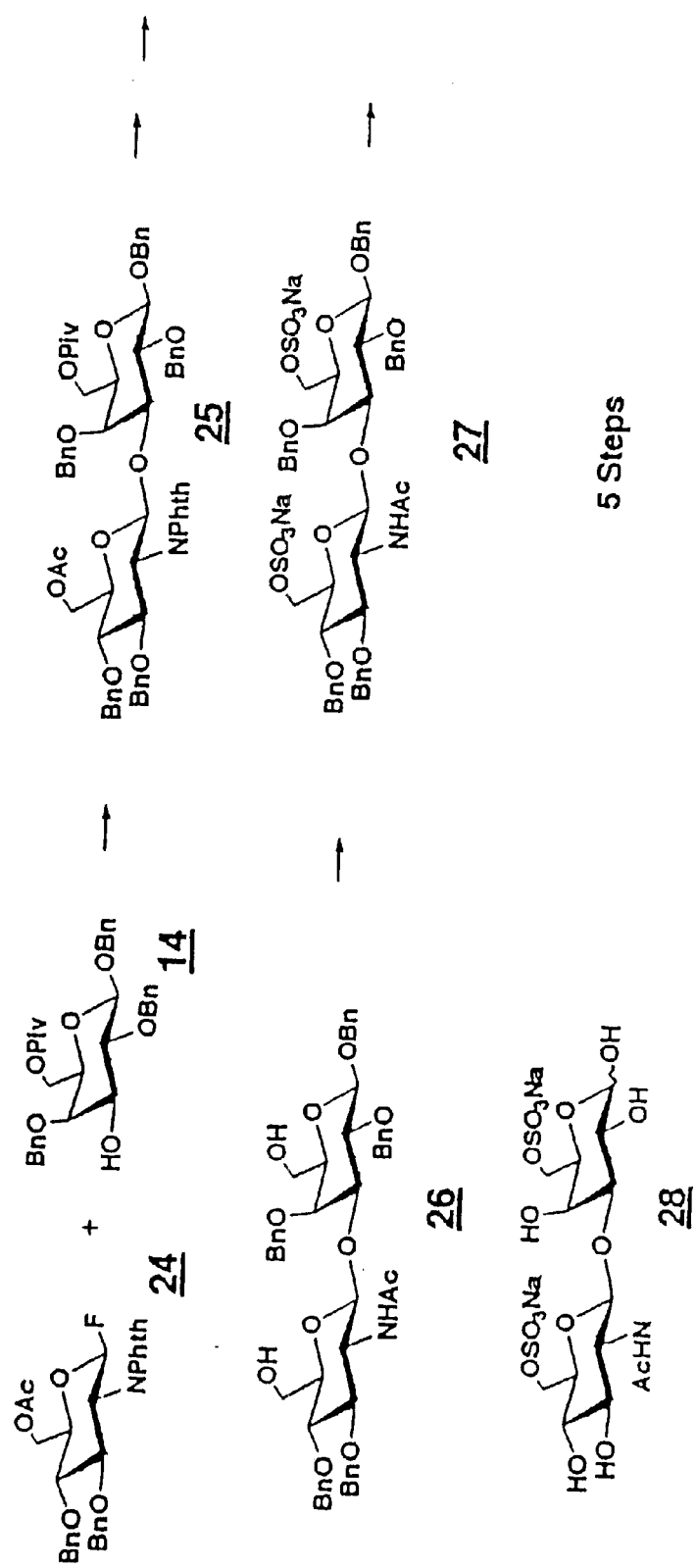
FIG. 4 outlines an example of the method for producing the oligosaccharide of the present invention.

Specifically, the oligosaccharide of the general formula (3) can be obtained by the method outlined in FIG. 4. That is, it can be obtained by a process comprising elimination of an acetyl group and a pivaloyl group (and substitution of a hydrogen atom) and substitution of an acetyl group for a phthaloyl group (Compound 26), sulfation (Compound 27), and debenzylation (Compound 28). Conditions for these steps may be suitably selected by those skilled in the art.

When one of $R^{10}$ and $R^{11}$ represents —$SO_3M$, the acyl group and the silyl group of $R^3$ and $R^7$ may be selected so that one of them can be selectively eliminated. For example, a levulinoyl group is selected as $R^3$ (monosaccharide of formula (7) or (10)), and a t-butyldiphenylsilyl group is selected as $R^7$ (monosaccharide of formula (8) or (11)). By selective elimination of the levulinoyl group (and substitution of a hydrogen atom for it), sulfation, and elimination of protective groups for other hydroxyl groups, an oligosaccharide in which only the hydroxyl group of the 6-position of the glucosamine residue has been sulfated (oligosaccharide of the formula (9)) can be obtained. By selective elimination of the t-butyldiphenylsilyl group (and substitution of a hydrogen atom for it), sulfation, and elimination of protective groups for hydroxyl groups, an oligosaccharide in which only the hydroxyl group of the 6-position of the galactose residue has been sulfated (oligosaccharide of the formula (12)) can be obtained.

The selective elimination of the acyl group or the silyl group (and the substitution of the hydrogen atom for it), the sulfation of the hydroxyl group formed by the elimination of the acyl group or the silyl group, the elimination of the aralkyl group, and the substitution of the acetyl group for the protective group for the amino group can be performed by known methods.

Figure 5:
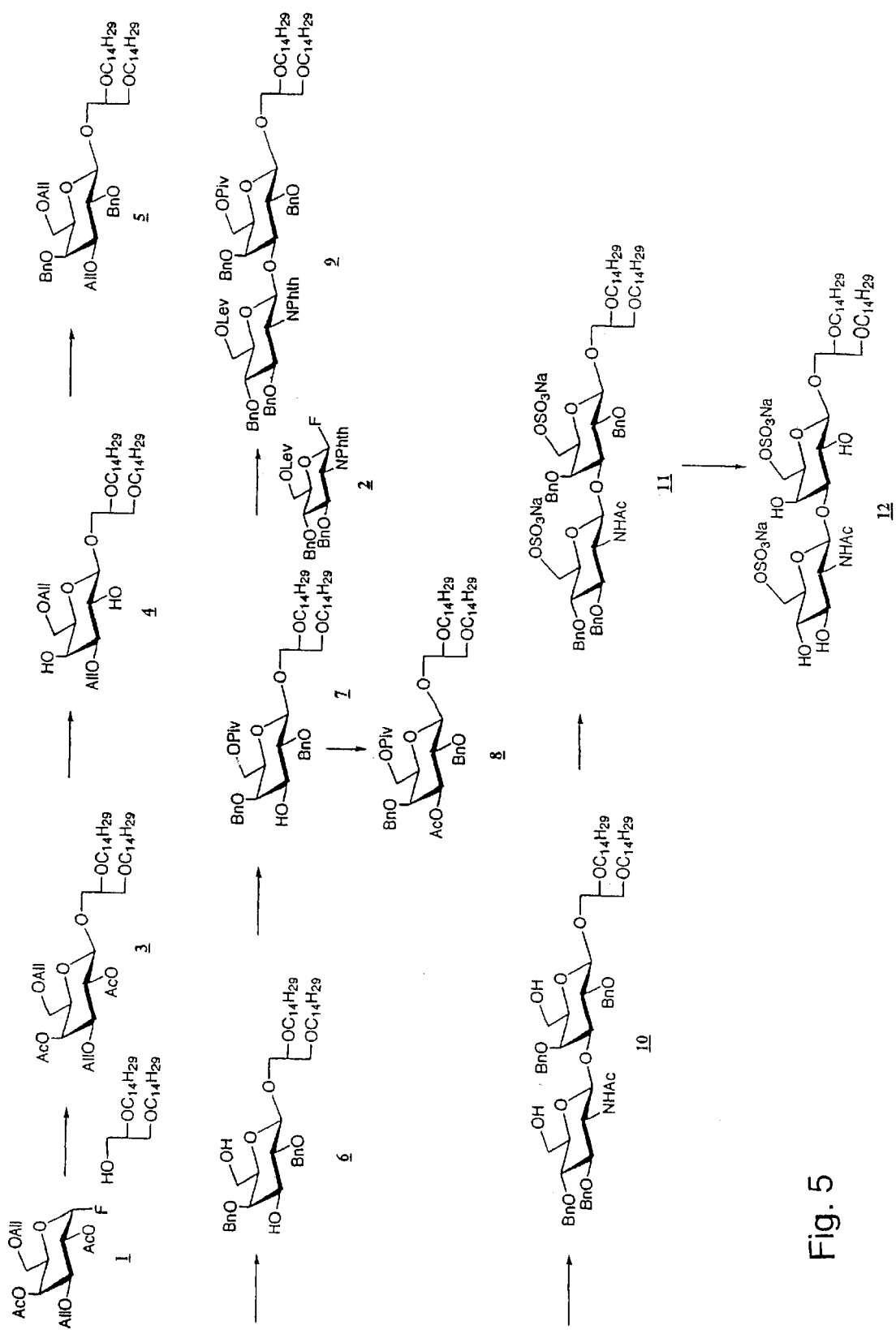
FIG. 5 outlines an example of the method for producing the oligosaccharide of the present invention.
Figure 6:
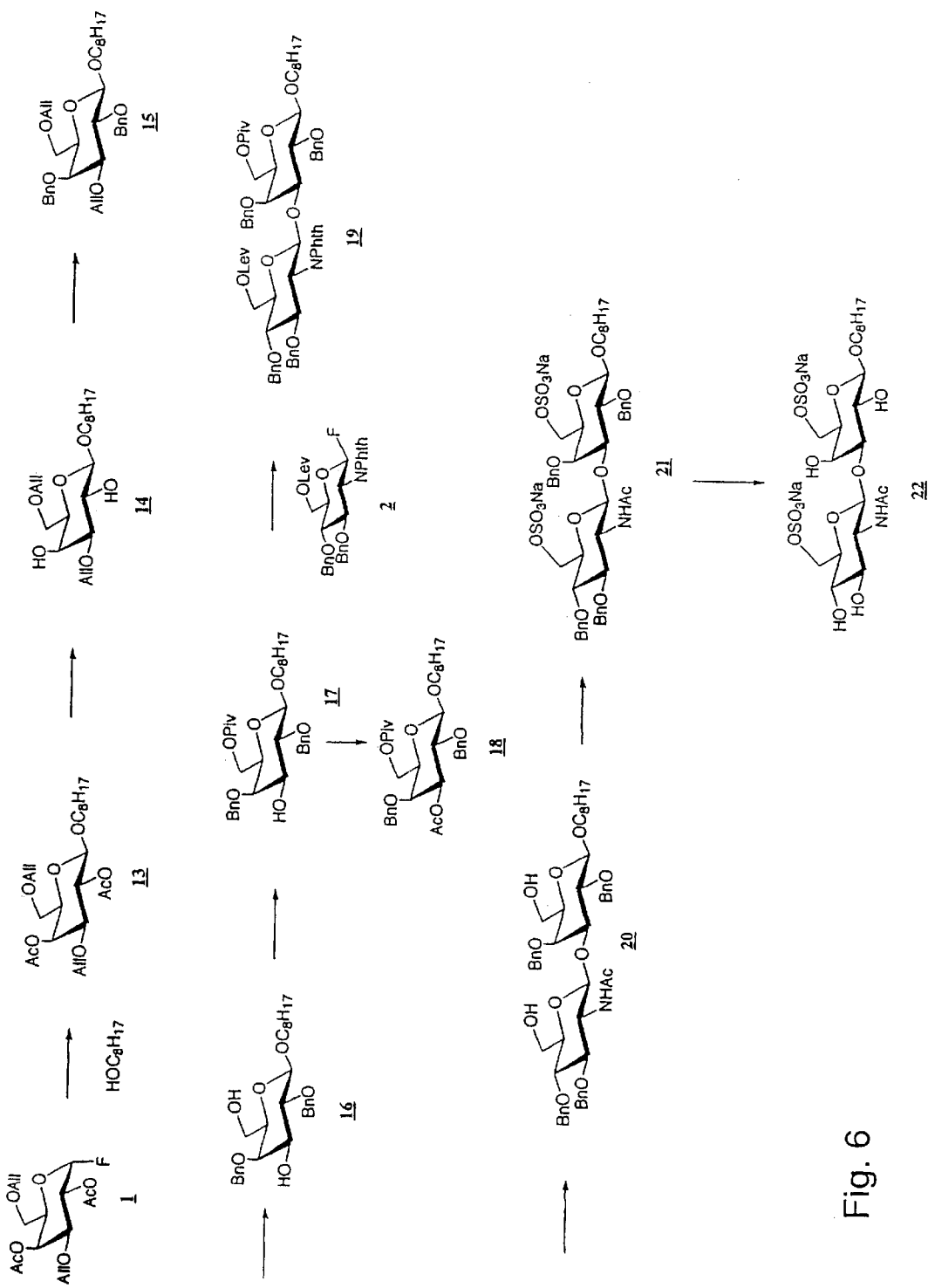
FIG. 6 outlines an example of the method for producing the oligosaccharide of the present invention.
Figure 7:
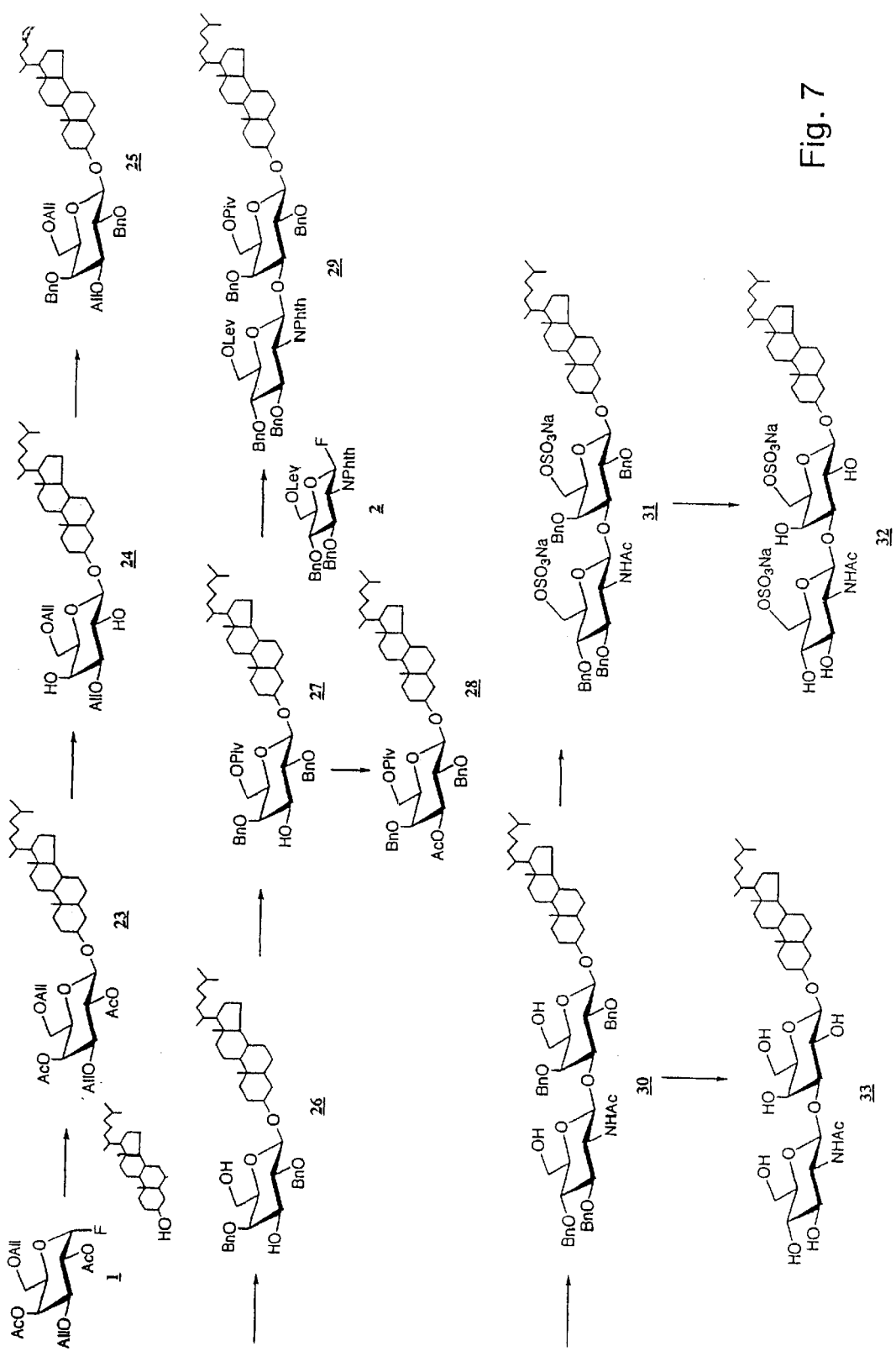
FIG. 7 outlines an example of the method for producing the oligosaccharide of the present invention.

Other examples of the method for producing the oligosaccharide represented by the general formula (3) by the glycosidic linkage formation between the monosaccharide represented by the general formula (1) and the monosaccharide represented by the general formula (2) and the like are shown in FIGS. 5 to 7.

FIG. 5 shows an example in which $R^9$ in the general formula (2) is an O-alkylglycerol residue (2,3-di-O-tetradecyl-sn-glycerol residue). FIG. 6 shows an example in which $R^9$ in the general formula (2) is an alkyl group (octyl group). FIG. 7 shows an example in which $R^9$ in the general formula (2) is a cholestanyl group. These can be performed by methods similar to the method described above. When $R^9$ is the other group or residue, the production can be performed by the similar method.

The obtained sulfated oligosaccharide may be in the form of a salt (that is, M in this oligosaccharide may be a monovalent cation), or it may not be in the form of a salt (that is, M in this oligosaccharide may be a proton). Examples of the salt include those mentioned in the section of <3> medicine of the present invention described below. However, it is preferably an alkali metal salt, particularly preferably a sodium salt. Further, the oligosaccharide may be in an ionized state.

According to the production method of the present invention, the aforementioned oligosaccharide can be produced with a high yield with fewer steps.

<2> Oligosaccharide of the Present Invention

The oligosaccharide of the present invention is the oligosaccharide represented by the general formula (13).

The substituents in the compounds represented by the general formula (13) are as follows.

$R^{16}$ and $R^{17}$ each independently represent a hydrogen atom or $—SO_3M$. However, the oligosaccharide wherein both of $R^{16}$ and $R^{17}$ are hydrogen atoms, Z is an oxygen atom and $R^{18}$ is a hydrogen atom or a cholestanyl group, and the oligosaccharide wherein $R^{16}$ represents $—SO_3M$, Z is an oxygen atom and both of $R^{17}$ and $R^{18}$ are hydrogen atoms are excluded.

$R^{18}$ represents a hydrogen atom, a 6-O-sulfated N-acetylglucosamine residue, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue. It is preferably a hydrogen atom, a 6-O-sulfated N-acetylglucosamine residue, an alkyl group, an O-alkylglycerol residue, or a cholestanyl group. These groups and residues are as described with respect to $R^9$. When $R^{18}$ in the general formula (13) is a hydrogen atom, the hydroxyl group constituted by $R^{18}$ may be at the β-position or α-position. When $R^{18}$ is a 6-O-sulfated N-acetylglucosamine residue, its glycosidic linkage is preferably a β-glycosidic linkage, more preferably a β-1,4-glycosidic linkage. When $R^{18}$ is the other group or residue, its glycosidic linkage is preferably β-glycosidic linkage.

Z represents an oxygen atom or $—NHCO—$. When $R^{18}$ is a biotin residue or a peptide residue, Z is preferably $—NHCO—$. When $R^{18}$ is the other group or residue, Z is preferably an oxygen atom.

The oligosaccharide of the present invention may be in the form of a salt (that is, M in this oligosaccharide may be a monovalent cation), or it may not be in the form of a salt (that is, M in this oligosaccharide may be a proton). Examples of the salt include those mentioned in the section of <3> medicine of the present invention described below. However, it is preferably an alkali metal salt, particularly preferably a sodium salt. Further, the oligosaccharide may be in an ionized state.

The oligosaccharide of the present invention whose $R^{18}$ is a hydrogen atom can be obtained by the aforementioned production method of the present invention. The oligosaccharide of the present invention whose $R^{18}$ is other than a hydrogen atom can be obtained by bonding a monosaccharide having an alkyl group, a glycerol residue, an O-alkylglycerol residue, an O-acylglycerol residue, a cholesterol residue, a cholestanyl group, a ceramide residue, a phospholipid residue, a biotin residue or a peptide residue with another monosaccharide as shown in FIGS. 5 to 7, or by bonding an oligosaccharide of the present invention whose $R^{18}$ is a hydrogen atom with glycerol, cholesterol, ceramide, biotin or peptide through a known glycosylation method.

The oligosaccharide of the present invention whose $R^{18}$ is a 6-O-sulfated N-acetylglucosamine residue can be produced by, for example, acidolysis of a known keratan sulfate oligosaccharide, or treating a known keratan sulfate oligosaccharide with an enzyme. For example, such an oligosaccharide can be produced by incubating a known keratan sulfate oligosaccharide, NeuAc~Galβ1-4GlcNAc(6S)β1-3Gal(6S)β1-4GlcNAc(6S) (wherein, Gal represents a galactose residue, GlcNAc represents N-acetylglucosamine residue, NeuAc represents N-acetylneuraminic acid residue, and 6S represents a 6-O-sulfate ester, and ~ represents α2,3 or α2,6 linkage; see WO96/16973) with an strong acid of around 0.2 N to eliminate the N-acetylneuraminic acid (sialic acid) residue, and then incubating the product with lactase (β-galactosidase) to eliminate the galactose residues. Details of these reactions will be described in the example mentioned below.

The oligosaccharide of the present invention or a pharmaceutically acceptable salt has a pharmacological activity, and can be used as a medicine.

<3> Medicine of the Present Invention

The medicine of the present invention contains the oligosaccharide of the present invention or a pharmaceutically acceptable salt thereof as an active ingredient.

The pharmaceutically acceptable salt means any pharmaceutically acceptable salts among, for example, alkali metal salts such as a sodium salt, a potassium salt and a lithium salt, alkaline earth metal salts such as a calcium salt, inorganic base salts such as an ammonium salt, organic base salts such as a diethanolamine salt, a cyclohexylamine salt and amino acid salts and so forth. But it is not limited to these.

The medicine of the present invention can be utilized, in particular, as an anti-allergy agent. When the oligosaccharide of the present invention is used as an anti-allergy agent, it is preferred that the hydroxyl group of the 6-position of the N-acetylglucosamine residue of a oligosaccharide of the present invention is sulfated (that is, $R^{16}$ in the general formula (13) is $—SO_3M$), and it is more preferred that both of the hydroxyl group at the 6-position of the galactose residue and the hydroxyl group at the 6-position of the N-acetyl glucosamine residue are sulfated (that is, both of $R^{16}$ and $R^{17}$ in the general formula (13) are $—SO_3M$).

The anti-allergy agent of the present invention is effective for any diseases involving allergy. More specifically, it can be used with the purpose of prevention or treatment of bronchial asthma, allergic interstitial pneumonia, allergic rhinitis, allergic conjunctivitis, atopic dermatitis and so forth.

The medicine of the present invention containing the oligosaccharide of the present invention in which the hydroxyl group at the 6-position of the galactose residue and the hydroxyl group at the 6-position of the N-acetylglucosamine residue are sulfated can be utilized, in particular, as an anti-inflammatory agent.

The anti-inflammatory agent of the present invention is effective for any diseases involving inflammation. More-specifically, it can be used with the purpose of prevention or treatment of rheumatoid arthritis, systemic lupus erythematosus, spondylitis deformans, arthrosis deformans, lumbago, for remission of inflammation and enlargement after surgical operations or external injuries, scapular periarthritis, temporomandibular arthrosis, peritenonitis, peritendinitis, inflammation of condylus humeri (tennis elbow), muscular ache, keratoconjunctivitis and so forth. The anti-inflammatory agent of the present invention exhibits anti-inflammatory activities including analgesic activity, antiphlogistic action, antipyretic action and so forth against these diseases due to the pharmacological activity of the active ingredient.

The medicine of the present invention can be used not only for treatment purpose in the literal sense of the term, but also for prevention, maintenance (prevention of aggravation), alleviation (improvement of symptoms) and so forth of diseases.

According to the present invention, an arbitrary dosage form can be selected depending on the nature or progression of disease of interest, administration route and so forth.

That is, the medicine of the present invention can be administered by injection (intravenous, intramuscular, subcutaneous, intracutaneous, intraperitoneal injections etc.), oral administration, transdermal administration, inhalation and so forth, and can be suitably formulated according to these administration routes. The dosage form that can be selected is not particularly limited, and it can be selected from a wide range including injection (solution, suspension, emulsion, solid to be dissolved upon use etc.), tablet, capsule, granule, powder, liquid, liposome inclusion, ointment, gel, powder for external application, spray, inhalation powder and so forth. For the preparation of these preparations, any ingredients commonly used for medicines including conventional excipients, stabilizing agents, binders, lubricants, emulsifiers, osmotic pressure regulators, pH regulators, coloring materials, disintegrating agents and so forth may be used.

The formulation amount of the active ingredient of the medicine of the present invention, the keratan sulfate oligosaccharide, and dose of the medicine of the present invention should be individually determined depending on the administration route, purpose of use, specific symptoms of patients, body weight of patients and the like, and they are not particularly limited.

In allergic diseases, antigens induce release of chemical transmitters from sensitized mast cells having IgE antibodies present in the respiratory tract or lungs. The chemical transmitters include histamine, eosinophilic chemotactic factor, SRS-A and so forth. They cause symptoms such as dyspnea, cough, attack etc. in asthma, and hemorrhagic pneumonia, edema, interstitial pneumonia, vasculitis etc. in lung diseases. They may rarely cause granuloma, and this disease often develops into pulmonary fibrosis. Allergic diseases are usually treated with antihistamines, steroids, and anti-allergy agents (inhibitors for release of chemical transmitters). However, as for antihistamines, weakness, feebleness, headache, vomition, dull headache, loss of appetite and so forth have been reported as side effects. In bronchial asthma, antihistamines suppress respiratory tract secretion because of the anti-choline activity and makes spitting and expectoration difficult, and therefore they are not used except for mild conditions. Moreover, they constitute a contraindication for patients of glaucoma and difficulty of urination. On the other hand, the main activity of steroids is considered to be anti-inflammatory activity, and they usually require extensive and continuous administration for the treatment of allergic diseases. Since steroids show critical side effects, they are principally used for cases that cannot be controlled by usual therapies. Furthermore, because anti-allergic agents may cause hepatopathy, hemorrhagic cystitis, and gastrointestinal injury, they require periodical inspection.

Thus, especially in the field of allergic diseases, effective therapies with less side effects have been required, and the medicine of the present invention provides such therapies.

In the medicine of the present invention (including the anti-allergy agent and the anti-inflammatory agent), preferred $R^{18}$ and Z are as described above.

As described above, according to the present invention, the keratan sulfate oligosaccharide having the galactose residue at the reducing end can be produced efficiently. In particular, there can be provided the keratan sulfate oligosaccharide in which the hydroxyl group(s) at the 6-position(s) of the galactose residue and/or N-acetylglucosamine residue are/is sulfated. The keratan sulfate oligosaccharides which have a galactose residue in which the hydroxyl group at the 6-position is sulfated at the reducing end and the like have an excellent pharmacological activity, and can provide a safe and effective novel pharmaceutical composition.

EXAMPLES

The present invention will be explained more specifically with reference to the following examples. However, the scope of the present invention is not limited by these.

Example 1
Synthesis of O-(2-Acetamido-2-deoxy-6-O-sulfo-β-D-glucopyranosyl)-(1→3)-O-6-O-sulfo-β-D-galactopyranose Disodium Salt O-(2-Acetamido-2-deoxy-6-O-sulfo-β-D-glucopyranosyl)(1→3)-O-6-O-sulfo-β-D-galactopyranose disodium salt was synthesized according to the scheme outlined in FIGS. 2–4. Methods commonly used for the syntheses in the following Examples were performed as follows. Silica gel column chromatography was performed by using Kiesegel 60 (MERCK). Thin layer chromatography was performed by using HPTLC-Fertigplatten Kieselgel 60 $F_{254}$ (MERCK). $^1$H-NMR spectra and $^{13}$C-NMR spectra were measured by using JNM-EX-400 (produced by JEOL Ltd.). As the internal standard, tetramethylsilane was used for measurement solvents of $CDCl_3$ and $CD_3OD$, and t-butanol for $D_2O$.

(1) Syntheses of Compounds 2 to Compound 14

Galactose synthons 2–9 were synthesized from galactose (Compound 1) according to the synthetic route reported by Ito et al. (Agric. Biol. Chem., 50, 3227 (1986)). The syntheses of Compounds 10–14 were performed as follows.

The numbers following each substance name represent the compound numbers in FIGS. 2 to 4.

(a) Benzyl 2,4-di-O-Acetyl-3,6-di-O-allyl-β-D-galactopyranoside (10)

Under nitrogen gas atmosphere, benzyl alcohol (18.4 ml, 178.8 mmol) and Compound 9 (2,4-di-O-acetyl-3,6-di-O-allyl-D-galactopyranosyl trichloroacetimidate, 21.84 g, 44.67 mmol) were added to a reaction container containing previously dried molecular sieve 4A (30.0 g), and stirred for 15 minutes under ice cooling. After the addition of trimethylsilyl trifluoromethanesulfonate (1.7 ml, 8.93 mmol) to the reaction mixture under ice cooling, and it was stirred at the same temperature for 4 hours. The reaction mixture was diluted with ethyl acetate, and neutralized by addition of triethylamine under ice cooling, and the solvent was evaporated under reduced pressure. The residue was purified by silica gel column chromatography (toluene:ethyl acetate=6:1) to obtain Compound 10 (18.6 g, 96%).

Rf: 0.51 (toluene:ethyl acetate=3:1); $C_{23}H_{30}O_8$ MW: 434.47; 400 MHz $^1$H-NMR (CDCl$_3$, TMS) δ: 2.037 (s, 3H, OAc), 2.146 (s, 3H, OAc), 4.445 (d, 1H, J=7.8 Hz, H-1), 5.461 (d, 1H, J=2.9 Hz, H-4), 5.715–5.914 (m, 2H, CH$_2$=CH×2), 7.200–7.400 (m, 5H, aromatic).

(b) Benzyl 3,6-di-O-Allyl-β-D-galactopyranoside (11)

Sodium methoxide (134 mg, 2.5 mmol) was added to a solution of Compound 10 (10.84 g, 24.9 mmol) in methanol (30 ml), and the mixture was stirred at room temperature under nitrogen gas atmosphere for 48 hours. The reaction mixture was neutralized with acetic acid, and the solvent was evaporated under reduced pressure. The residue was purified by silica gel column chromatography (toluene:ethyl acetate=4:1) to obtain Compound 11 (6.8 g, 78%).

Rf: 0.27 (toluene:ethyl acetate=2:1); $C_{19}H_{26}O_6$ MW: 350.40.

(c) Benzyl 3,6-di-O-Allyl-2,4-di-O-benzyl-β-D-galactopyranoside (12)

Under nitrogen gas atmosphere and ice cooling, benzyl bromide (11.4 ml, 95.5 mmol) was added to a mixture of 60% sodium hydride (3.8 g, 95.5 mmol), Compound 11 (6.7 g, 19.1 mmol) and dimethylformamide (20 ml), and the mixture was stirred for 18 hours. Methanol was added to the reaction mixture under ice cooling and stirred for 1 hour, and the solvent was evaporated under reduced pressure. The residue was diluted with diethyl ether, washed successively with water and saturated brine, and dried over magnesium sulfate. The solvent was evaporated under reduced pressure. The obtained residue was purified by silica gel column chromatography (n-hexane:ethyl acetate=10:1–9:1) to obtain Compound 12 (9.1 g, 90%).

Rf: 0.27 (toluene:ethyl acetate=10:1); $C_{33}H_{38}O_6$ MW: 530.63; 400 MHz $^1$H-NMR (CDCl$_3$, TMS) δ: 3.424 (dd, 1H, J=2.9, 9.8 Hz, H-3), 3.829 (dd, 1H, J=7.8, 9.8 Hz, H-2), 3.861 (d, 1H, J=2.9 Hz, H-4), 4.453 (d, 1H, J=7.8 Hz, H-1), 5.805–5.984 (m, 2H, CH$_2$=CH×2), 7.200–7.450 (m, 15H, aromatic).

(d) Benzyl 2,4-di-O-Benzyl-β-D-galactopyranoside (13)

Under hydrogen gas atmosphere, a solution of Compound 12 (8.9 g, 16.7 mmol) in tetrahydrofuran (80 ml) was added to a solution of activated iridium complex (Ir(CoD)(PMePh$_2$)$_2$PF$_6$, 287 mg, 0.34 mmol) in tetrahydrofuran (60 ml) at room temperature, and the mixture was stirred for 7 hours. Subsequently, water (100 ml) and iodine (8.5 g, 67.1 mmol) were added to the reaction mixture, and it was stirred for 15 hours. The reaction mixture was diluted with ethyl acetate, washed successively with saturated sodium thiosulfate solution, saturated aqueous sodium hydrogencarbonate, and saturated brine, and dried over magnesium sulfate, and the solvent was evaporated under reduced pressure. The obtained residue was recrystallized (ethanol/dichloromethane/diethyl ether) to obtain Compound 13 (7.4 g, 97%).

Rf: 0.34 (n-hexane:ethyl acetate=1:1); $C_{27}H_{30}O_6$ MW: 450.51.

(e) Benzyl 2,4-di-O-Benzyl-6-O-pivaloyl-β-D-galactopyranoside (14)

Under nitrogen gas atmosphere, pivaloyl chloride (4.2 ml, 35.7 mmol) was added to a solution of Compound 13 (7.3 g, 16.2 mmol) in pyridine (50 ml) at 0° C., and the mixture was stirred for 70 minutes. Methanol was added to the reaction mixture, and the mixture was stirred for 40 minutes, and the solvent was evaporated under reduced pressure. The residue was purified by silica gel column chromatography (toluene:ethyl acetate=6:1) to obtain Compound 14 (7.81 g, 90%).

Rf: 0.45 (toluene:ethyl acetate=6:1); $C_{32}H_{38}O_7$ MW: 534.62; 400 MHz $^1$H-NMR (CDCl$_3$, TMS) δ: 1.202 (s, 9H, OPiv), 2.326 (bs, 1H, OH), 3.628–3.708 (m, 3H, H-2, H-3 and H-5), 3.786 (d, 1H, J=3.9 Hz, H-4), 4.142 (dd, 1H, J=6.4, 10.7 Hz, H-6), 4.352 (dd, 1H, J=6.8, 11.2 Hz, H-6'), 4.448 (d, 1H, J=7.3 Hz, H-1), 6.650–7.150 (m, 15H, aromatic).

(2) Syntheses of Compound 16 to Compound 24

Glucosamine synthons 16–20 were synthesized from glucosamine (Compound 15) according to the synthetic route reported by Nakano et al. (Tetrahedron Lett., 31, 1597 (1990)). Compounds 21–24 were synthesized as follows.

(f) p-Methoxyphenyl 3,4-di-O-Benzyl-2-deoxy-2-phthalimido-β-D-glucopyranoside (21)

To a reaction container containing previously dried molecular sieve 4A (60.0 g), borane-trimethylamine complex (75.0 g, 1028 mmol), a solution of Compound 20 (21.0 g, 35.4 mmol) in dichloromethane (200 ml) and diethyl ether (80 ml) were added, and the mixture was stirred for 15 minutes under nitrogen gas atmosphere. The reaction container was cooled to 0° C., and anhydrous aluminium chloride (20.0 g, 150 mmol) was added to the reaction mixture portionwise over 1.5 hours, and the mixture was stirred at 0° C. for 2.5 hours. The reaction mixture was filtrated through Celite, and the filtrate was diluted with ethyl acetate, washed successively with 1 N sulfuric acid aqueous solution, water, saturated aqueous sodium hydrogencarbonate, and saturated brine. The filtrate was dried over magnesium sulfate, and the solvent was evaporated under reduced pressure. The obtained residue was purified by silica gel column chromatography (toluene:ethyl acetate=4:1) to obtain Compound 21 (14.5 g, 69%).

Rf: 0.40 (toluene:ethyl acetate=3:1); $C_{35}H_{33}N_1O_8$ MW: 595.62; 400 MHz $_1$H-NMR (CDCl$_3$+CD$_3$OD, TMS) δ: 3.620–3.662 (m, 1H, H-5), 3.706 (s, 3H, OMe), 3.783–3.849 (m, 2H, H-4 and H-6), 3.939 (dd, 1H, J=2.4, 12.2 Hz, H-6'), 4.351 (dd, 1H, J=8.3, 10.7 Hz, H-2), 4.435 (dd, 1H, J=8.3, 10.7 Hz, H-3), 5.693 (d, 1H, J=8.3 Hz, H-1), 6.650–7.900 (m, 18H, aromatic).

(g) p-Methoxyphenyl 6-O-Acetyl-3,4-di-O-benzyl-2-deoxy-2-phthalimido-β-D-glucopyranoside (22)

Under nitrogen gas atmosphere, acetic anhydride (200 ml) and DMAP (catalytic amount) were added to a solution of Compound 21 (10.5 g, 17.6 mmol) in pyridine (200 ml), and the mixture was stirred for 20 hours. Ethanol was added to the reaction mixture, and it was stirred for 20 minutes. The solvent was then evaporated under reduced pressure. The residue was purified by silica gel column chromatography (toluene:ethyl acetate=4:1) to obtain Compound 22 (9.6 g, 85%).

Rf: 0.51 (toluene:ethyl acetate=4:1); $C_{37}H_{35}N_1O_9$ MW: 637.66; 400 MHz $^1$H-NMR (CDCl$_3$, TMS) δ: 2.062 (s, 3H, OAc), 3.680 (s, 3H, OMe), 3.759–3.817 (m, 2H, H-4 and H-5), 4.296 (dd, 1H, J=4.4, 12.2 Hz, H-6), 5.631 (d, 1H, J=7.8 Hz, H-1), 6.650–7.900 (m, 18H, aromatic).

(h) 6-O-Acetyl-3,4-di-O-benzyl-2-deoxy-2-phthalimido-D-glucopyranose (23)

Compound 22 (9.0 g, 14.1 mmol) was dissolved in acetonitrile:water (4:1, 400 ml). Ammonium cerium (IV) nitrate (20.1 g, 36.7 mmol) was added thereto, and the mixture was stirred vigorously for 40 minutes at room temperature. The reaction mixture was diluted with ethyl acetate, washed successively with water, saturated aqueous sodium hydrogencarbonate, and saturated brine, and dried over magnesium sulfate. The solvent was evaporated under reduced pressure. The residue was purified by silica, gel column chromatography (toluene:ethyl acetate=2.5:1) to obtain Compound 23 (6.1 g, 81%).

Rf: 0.23 (toluene:ethyl acetate=2:1); $C_{30}H_{29}N_1O_8$ MW: 531.54; 400 MHz $^1$H-NMR (CDCl$_3$+D$_2$O, TMS) δ: 2.074 (s, 3H, OAc), 3.680 (t, 3H, J=9.3 Hz, H-4), 3.739–3.772 (m, 1H, H-5), 4.100 (dd, 1H, J=8.8, 10.8 Hz, H-2), 4.240 (dd, 1H, J=3.9, 11.2 Hz, H-6), 5.386 (d, 1H, J=8.3 Hz, H-1), 6.650–7.900 (m, 14H, aromatic).

(i) 6-O-Acetyl-3,4-di-O-benzyl-2-deoxy-2-phthalimido-β-D-glucopyranosyl Fluoride (24)

Under nitrogen gas atmosphere, diethylaminosulfur trifluoride (5.8 ml, 43.9 mmol) was added to a solution of Compound 23 (5.95 g, 11.2 mmol) in 1,2-dichloroethane (50 ml) under ice cooling, and the mixture was stirred for 2 hours. The reaction mixture was diluted with ethyl acetate, washed successively with saturated aqueous sodium hydrogencarbonate and saturated brine, and dried over magnesium sulfate. Then, the solvent was evaporated under reduced pressure. The residue was purified by silica gel column chromatography (toluene:ethyl acetate=4:1) to obtain Compound 24 (5.9 g, 99%).

Rf: 0.68 (toluene:ethyl acetate=2:1); $C_{30}H_{28}N_1O_7F_1$ MW: 533.53; 400 MHz $^1$H-NMR (CDCl$_3$, TMS) δ: 2.097 (s, 3H, OAc), 3.859 (dd, 1H, J=8.3, 9.8 Hz, H-4), 3.800–3.840 (m, 1H, H-5), 5.810 (d, 0.5H, J=7.8 Hz, H-1β), 5.943 (d, 0.5H, J=7.8 Hz, H-1β), 6.800–7.800 (m, 14H, aromatic).

(3) Synthesis of Compound 28 from Compound 14 and Compound 24

Compounds 25–28 were synthesized as follows.

(j) Benzyl O-(6-O-Acetyl-3,4-di-O-benzyl-2-deoxy-2-phthalimido-β-D-glucopyranosyl)-(1→3)-O-2,4-di-O-benzyl-6-O-pivaloyl-β-D-galactopyranoside (25)

Under nitrogen gas atmosphere, silver triflate (7.23 g, 28.2 mmol), hafnocene dichloride (5.4 g, 14.1 mmol) and 1,2-dichloroethane (20 ml) were added to a reaction container containing previously dried molecular sieve 4A (20.0 g), and the mixture was stirred for 20 minutes under ice cooling. The reaction container was cooled to −23° C., and then a solution of Compound 24 (5.8 g, 10.8 mmol) and Compound 14 (5.4 g, 10.0 mmol) in 1,2-dichloroethane (45 ml) were added to the mixture, and it was stirred at −23° C. for 1.5 hours. The reaction mixture was diluted with ethyl acetate, and triethylamine was added thereto under ice cooling. The mixture was stirred for 20 minutes, and filtrated through Celite. The filtrate was diluted with ethyl acetate, washed successively with saturated aqueous sodium hydrogencarbonate and saturated brine, and dried over magnesium sulfate. Then, the solvent was evaporated under reduced pressure. The residue was purified by silica gel column chromatography (toluene:ethyl acetate=9:1) and recrystallized to obtain Compound 25 (9.3 g, 82%).

Rf: 0.39 (toluene:ethyl acetate=8:1); $C_{62}H_{65}N_1O_{14}$ MW: 1048.15; 400 MHz $^1$H-NMR (CDCl$_3$, TMS) δ: 1.173 (s, 9H, OPiv), 1.986 (s, 3H, OAc), 3.859 (bd, 1H, J=2.5 Hz, H-4), 4.063 (dd, 1H, J=5.9, 11.2 Hz), 5.454 (d, 1H, J=8.3 Hz, H-1), 6.800–7.800 (m, 24H, aromatic).

(k) Benzyl O-(2-Acetamido-3,4-di-O-benzyl-2-deoxy-β-D-glucopyranosyl)-(1→3)-O-2,4-di-O-benzyl-β-D-galactopyranoside (26)

Ethylenediamine (170 ml) was added to a solution of Compound 25 (8.0 g, 7.6 mmol) in 1-butanol (200 ml), and the mixture was stirred at 98° C. for 46 hours. The solvent of the reaction mixture was evaporated under reduced pressure. Toluene and methanol were added to the residue, and the solvent was evaporated under reduced pressure. The residue was dissolved in pyridine (200 ml), and DMAP (catalytic amount) and acetic anhydride (150 ml) were added thereto. The mixture was stirred for two days at room temperature. The solvent of the reaction mixture was evaporated, and the residue was subjected to azeotropy with toluene and ethanol. The obtained residue was purified by silica gel column chromatography (toluene:ethyl acetate= 4:1) to obtain a mixture of two components (6.84 g). To a solution of this mixture in methanol (100 ml), sodium methoxide (769 mg, 14.3 mmol) was added, and the mixture was stirred at room temperature under nitrogen gas atmosphere for 60 hours. The reaction mixture was neutralized with Amberlist 15 and filtered, and the filtrate was evaporated under reduced pressure. The obtained residue was recrystallized (dichloromethane/isopropyl ether) to obtain Compound 26 (6.0 g, 94%).

Rf: 0.33 (toluene:ethyl acetate=1:3); $C_{49}H_{55}N_1O_{11}$ MW: 833.94; 400 MHz $^1$H-NMR (CDCl$_3$+CD$_3$OD, TMS) δ: 1.557 (s, 3H, NAc), 4.438 (d, 1H, J=7.3 Hz, H-1), 4.784 (d, 1H, J=8.3 Hz, H-1), 7.200–7.450 (m, 20H, aromatic). 100 MHz $^{13}$C-NMR (CDCl$_3$+CD$_3$OD, TMS) δ: 22.92 (Me—CO), 61.44, 61.64 (C-6×2), 101.73 (C-1), 102.60 (C-1), 170.29 (Me—CO).

(l) Benzyl O-(2-Acetamido-3,4-di-O-benzyl-2-deoxy-6-O-sulfo-β-D-glucopyranosyl)-(1→3)-O-2, 4-di-O-benzyl-6-O-sulfo-β-D-galactopyranoside Disodium Salt (27)

Under nitrogen gas atmosphere, a mixture of Compound 26 (212.5 mg, 0.255 mmol) and sulfur trioxide-triethylamine complex (184.7 mg, 1.02 mmol) were dissolved in dimethylformamide (1.0 ml), and the mixture was stirred for 1 hour at 50° C. The reaction mixture was purified with Sephadex LH-20 (chloroform:methanol=1:1) as it was, and the saccharide fraction was concentrated. The obtained residue was dissolved in methanol (4 ml). Dowex 50 (Na$^+$, 4 g) was added thereto, and the mixture was stirred for 12 hours to replace the counter ion with sodium ion. Further, the obtained residue was purified by silica gel column chromatography (chloroform:methanol=4:1), and further purified with Sephadex LH-20 (chloroform:methanol=1:1) to remove the silica gel. Thus, Compound 27 (252 mg, 95%) was obtained.

Rf: 0.53 (chloroform:methanol=3:1); $C_{49}H_{53}N_1O_{17}S_2Na_2$ MW: 1038.03; 400 MHz $^1$H-NMR (CDCl$_3$+CD$_3$OD, TMS) δ: 1.621 (s, 3H, NAc), 7.200–7.450 (m, 20H, aromatic), 100 MHz $^{13}$C-NMR (CDCl$_3$+CD$_3$OD, TMS) δ: 22.14 (Me—CO), 66.25, 66.61 (C-6×2), 102.04 (C-1×2), 170.98 (Me—CO).

(m) O-(2-Acetamido-2-deoxy-6-O-sulfo-β-D-glucopyranosyl)-(1→3)-O-6-O-sulfo-β-D-galactopyranose Disodium Salt (28)

20% Palladium hydroxide/carbon (268 mg) was added to a solution of Compound 27 (236.8 mg, 0.228 mmol) in methanol/water (2:1, 6 ml). The inside of the reaction system was replaced with hydrogen, and the mixture was stirred at room temperature for 17 hours. The reaction mixture was filtered through Celite, and the residue was washed with water. Then, the filtrate and the wash were combined, and the solvent was evaporated under reduced pressure. The obtained residue was purified with Sephadex G-25 (water) to obtain Compound 28 (131 mg, 98%).

Rf: 0.28 (1-butanol:ethanol:water=2:2:1); $C_{14}H_{23}N_1O_{17}S_2Na_2$ MW: 587.44; 400 MHz $^1$H-NMR ($D_2O$, t-BuOH, at 50° C.) δ: 2.029 (s, 3H, NAc), 4.580 (d, 0.55H, J=8.3 Hz, H-1αβ), 4.727 (d, 0.55H, J=8.3 Hz, H-1bβ), 4.742 (d, 0.45H, J=8.3 Hz, H-1bα), 5.232 (d, 0.45H, J=3.4 Hz, H-1aα), 100 MHz $^{13}$C-NMR ($D_2O$, t-BuOH, at 50° C.) δ: 25.04 (Me—CO), 69.81 (C-6b), 70.70 (C-6aβ), 70.94 (C-6 aα), 95.21 (C-1aα), 99.21 (C-1aβ), 105.39 (C-1b), 177.74 (Me—CO).

Example 2

Production of O-(2-Acetamido-2-deoxy-6-O-sulfo-β-D-glucopyranosyl)-(1→3)-O-(6-O-sulfo-β-D-galactopyranosyl)-(1→4)-O-2-acetamido-2-deoxy-6-O-sulfo-β-D-glucopyranose Trisodium Salt
(Referred to as Sodium Salt of G4L4 Hereinafter)

NeuAc~Galβ1-4GlcNAc(6S)β1-3Gal(6S)β1-4GlcNAc (6S) (wherein, Gal represents a galactose residue, GlcNAc represents an N-acetylglucosamine residue, NeuAc represents an N-acetylneuraminic acid residue, and 6S represents 6-O-sulfate ester, and ~ represents α2,3 or α2,6 linkage; see WO96/16973, 1 g) was dissolved in 10 ml of 0.1 M sulfuric acid, and the solution was incubated at 50° C. for 22 hours to cleave the N-acetylneuraminic acid residue (sialic acid residue). The solution after the reaction was adjusted to pH 5 by addition of a small amount of 1 M NaOH, and 1 ml of 0.5 M sodium acetate buffer, pH 4.5 and 25 μl of 20% sodium azide were added thereto. Lactase (produced by Keiai Kasei, 5000 U) was added to the mixture, and it was incubated at 37° C. for 22 hours to cleave the galactose residues. The reaction solution was diluted 5 times with distilled water, and applied to a Muromac column (Muromachi Kagaku Kogyo, 2.5×24 cm) equilibrated with 1 M NaCl. A salt concentration gradient of from 1 M NaCl (500 ml) to 2.5 M NaCl (500 ml) was loaded on the column, and the eluate was collected as 5-ml fractions. The eluted fractions were analyzed by capillary electrophoresis, and the elution fractions of G4L4 were confirmed. The fractions containing G4L4 were combined and concentrated to about 10 ml on a rotary evaporator. The concentrated solution was applied on a Cellulofine GCL25sf column (Seikagaku corporation, 3×60 cm) equilibrated with distilled water, and eluted with distilled water. The eluted fractions collected as 10-ml fractions were analyzed by capillary electrophoresis to confirm the elution fractions of G4L4. The fractions containing G4L4 were combined and concentrated to about 20 ml on a rotary evaporator. The concentrate was filtered through an ultrafiltration membrane of molecular weight cut of 10000 to eliminate endotoxins, and lyophilized to obtain a final sample.

The final sample showed a single peak in the capillary electrophoresis analysis. Its hexose content and sulfate content were measured to be 0.84 and 0.91, respectively, relative to the theoretical value defined to be 1.

Further, when the final sample was analyzed by high performance liquid chromatography under the following conditions, it showed a single peak at a retention time of 16.4 minutes.

Column: YMC-Pack Polyamine II (4.6×250 mm, produced by YMC Co., Ltd.)

Column temperature: 35° C.

Eluate: 150 mM sodium dihydrogenphosphate

Flow rate: 1 ml/minute

Measurement wavelength: 210 nm

Sample: 10 mg/ml G4L4 (the final sample)

The results of NMR analysis of the final sample are shown below.

400 MHz $^1$H-NMR ($D_2O$, t-BuOH, at 22.9° C.) δ: 2.024 (s, 3H, NAc), 2.030 (s, 3H, NAc), 4.526 (d, 1H, $J_{1,2}$=7.8 Hz, H-1b), 4.699 (d, 1H, $J_{1,2}$=8.8 Hz, H-1c), 4.729 (d, 0.4H, $J_{1,2}$=7.8 Hz, H-1aβ), 5.211 (d, 0.6H, $J_{1,2}$=2.5 Hz, H-1aα)

100 MHz $^{13}$C-NMR($D_2O$, t-BuOH, at 26.0° C.) δ: 24.74 (NHCO$\underline{C}H_3$), 25.05 (NHCO$\underline{C}H_3$), 69.62 (C-6a or b or c), 69.77 (C-6b or c or a), 70.57 (C-6c or a or b), 93.31 (C-1aα), 97.82 (C-1aβ), 105.80 (C-1b or c), 105.91 (C-1c or b)

Example 3

Synthesis of 2-Acetamido-2-deoxy-6-O-sulfo-β-D-glucopyranosyl-(1→3)-6-O-sulfo-β-D-galactopyranosyl-(1→1)-2,3-di-O-tetradecyl-sn-glycerol Disodium Salt 2-Acetamido-2-deoxy-6-O-sulfo-β-D-glucopyranosyl-(1→3) -6-O-sulfo-β-D-galactopyranosyl-(1→1)-2,3-di-O-tetradecyl-sn-glycerol disodium salt was synthesized according to the scheme outlined in FIG. 5.

The numbers after the substance names represent numbers of compounds in FIG. 5.

(a) 2,4-di-O-Acetyl-3,6-di-O-allyl-β-D-galactopyranosyl-(1→1)-2,3-di-O-tetradecyl-sn-glycerol (3)

2,3-Di-O-tetradecyl-sn-glycerol (500 mg, 1.03 mmol), cyclopentadiene hafnonium dichloride (782 mg, 2.68 mmol), silver triflate (1.06 g, 5.36 mmol) and molecular sieve 4A (1.8 g) were suspended in 1,2-dichloroethane (3.0 ml), stirred at room temperature under argon gas flow, and cooled to −15° C. Compound 1 (536 mg, 1.55 mmol) was added thereto, and the mixture was stirred for 2.5 hours. The reaction mixture was neutralized by addition of triethylamine, diluted with ethyl acetate, filtered through Celite. The filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 3 (716.7 mg, 85.8%).

Rf: 0.58 (toluene:AcOEt=6:1); $C_{47}H_{85}O_{10}$ MW: 810.179; $^1$H-NMR (CDCl$_3$) δ: 5.887 (m, 1H, Allyl), 5.816 (m, 1H, Allyl), 5.500 (d, 1H, J=2.4 Hz, H-4), 5.108 (dd, 1H, J=8.3, 9.9 Hz, H-2), 4.474 (d, 1H, J=8.3 Hz, H-1), 2.165, 2.015 (2s, 6H, 2Ac), 0.912 (t, 6H, J=6.3 Hz, 2CH$_3$).

(b) 3,6-di-O-Allyl-2,4-di-O-benzyl-β-D-galactopyranosyl-(1→1)-2,3-di-O-tetradecyl-sn-glycerol (5)

Compound 3 (430 mg, 0.531 mmol) was dissolved in a mixture of methanol and tetrahydrofuran (1:1, 4 mL). 1 N Sodium hydroxide solution (0.8 mL) was added thereto, and the mixture was stirred at room temperature for one day. Then, the reaction mixture was neutralized with Amberlist 15E (H$^+$) type, and filtered through Celite, and the filtrate; was evaporated. The residue was purified by silica gel column chromatography (toluene:AcOEt=5:2) to obtain Compound 4 (377.9 mg, 98.0%).

Rf: 0.43 (toluene:AcOEt=2:1).

Then, Compound 4 (778 mg, 1.072 mmol) was dissolved in N,N-dimethylformamide (3 ml). Sodium hydride (308 mg, 6.99 mmol) was added thereto, and the mixture was stirred at −15° C. under argon gas flow. Then, benzyl bromide (0.84 ml, 6.99 mmol) was added to the reaction mixture, and it was stirred for 3 hours while the temperature was gradually raised to room temperature. After addition of methanol to the reaction, it was neutralized, diluted with ethyl acetate, and washed successively with saturated aqueous sodium hydrogencarbonate and saturated brine. The ethyl acetate layer was;dried over magnesium sulfate, and the solvent was evaporated under reduced pressure. The residue was purified by silica gel column chromatography (hexane:AcOEt=12:1) to obtain Compound 5 (864 mg, 89%).

Rf: 0.67 (hexane:AcOEt=6:1); $C_{57}H_{93}O_8$ MW: 906.354; $^1$H-NMR (CDCl$_3$) δ: 5.845 (m, 1H, Allyl), 5.771 (m, 1H, Allyl), 4.859 (d, 1H, J=11.7 Hz, Bn), 4.816 (d, 1H, J=10.8 Hz, Bn), 4.665 (d, 1H, J=10.7 Hz, Bn), 4.572 (d, 1H, J=11.7 Hz, Bn), 4.272 (d, 1H, J=7.3 Hz, H-1), 3.773 (d, 1H, J=2.5 Hz, H-4), 3.660 (dd, 1H, J=7.8, 9.8 Hz, H-2), 0.801 (t, 6H, J=6.4 Hz, 2CH$_3$).

(c) 2,4-di-O-Benzyl-β-D-galactopyranosyl-(1→1)-2,3-di-O-tetradecyl-sn-glycerol (6)

Iridium complex (1,5-cyclooctadiene bis(methyldiphenylphosphine)iridium hexafluorophosphate, 112 mg, 0.096 mmol) was suspended in tetrahydrofuran (5 mL), and activated by stirring under H$_2$ flow. To this solution, Compound 5 (864 mg, 0.95 mmol) dissolved in tetrahydrofuran (5 mL) was added, and the mixture was stirred at room temperature for 2 hours under argon gas flow. Then, iodine (484 mg), water (24.7 mL) and tetrahydrofuran (15 mL) were added thereto, and the mixture was further stirred at room temperature for 2 hours. The reaction mixture was diluted with chloroform, and washed successively with saturated sodium thiosulfate solution, saturated aqueous sodium hydrogencarbonate, and saturated brine. The chloroform layer was dried over magnesium sulfate, and the solvent was evaporated under reduced pressure. The residue was purified by silica gel column chromatography (toluene:EtOAc=5:2) to obtain Compound 6 (686.6 mg, 87.1%).

Rf: 0.32 (toluene:AcOEt=2:1); $C_{51}H_{85}O_8$ MW: 826.225; $^1$H-NMR (CDCl$_3$) δ: 4.991 (d, 1H, J=11.2 Hz, Bn), 4.834 (d, 1H, J=11.7 Hz, Bn), 4.658 (d, 2H, J=11.2 Hz, 2Bn), 4.385 (d, 1H, J=7.3 Hz, H-1), 3.778 (d, 1H, J=2.4 Hz, H-4), 0.881 (t, 6H, J=6.8 Hz, 2CH$_3$).

(d) 2,4-di-O-Benzyl-6-O-pivaloyl-β-D-galactopyranosyl-(1→1)-2,3-di-O-tetradecyl-sn-glycerol (7)

Compound 6 (687 mg, 0.831 mmol) was dissolved by addition of pyridine (12 mL). Pivaloyl chloride (130 μl, 1.08 mmol) was added to the solution, and the mixture was stirred at −5° C. for 1 hour. Pivaloyl chloride (130 μl, 1.08 mmol) was further added thereto, and the mixture was stirred at −5° C. for 1 hour. The reaction mixture was diluted with ethyl acetate, then filtered through Celite, and washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 7 (716.6 mg, 94.7%).

Rf: 0.57 (toluene:AcOEt=6:1); $C_{56}H_{93}O_9$ MW: 910.342; $^1$H-NMR (CDCl$_3$) δ: 4.991 (d, 1H, J=11.7 Hz, Bn), 4.855 (d, 1H, J=11.7 Hz, Bn), 4.650 (d, 1H, J=11.2 Hz, Bn), 4.646 (d, 1H, J=11.7 Hz, Bn), 4.365 (d, 1H, J=7.3 Hz, H-1), 4.302 (dd, 1H, J=6.8, 11.8 Hz, H-6), 4.109 (dd, 1H, J=6.4, 11.2 Hz, H-6'), 3.775 (d, 1H, J=2.4 Hz, H-4), 1.179 (s, 9H, piv), 0.879 (t, 6H, J=6.8 Hz, 2CH$_3$).

(e) 3-O-Acetyl-2,4-di-O-benzyl-6-O-pivaloyl-β-D-galactopyranosyl-(1→1)-2,3-di-O-tetradecyl-sn-glycerol (8)

Compound 7 -(10.8 mg, 11.9 μmol) was dissolved by addition of pyridine (1 mL). Acetic anhydride (0.5 mL) was added to the solution, and the mixture was stirred at room temperature for 1 hour. The solvent was subjected to azeotropy with toluene, and then the residue was purified with Sephadex LH-20 (CHCl$_3$:MeOH=1:2) to obtain Compound 8 (11.3 mg, qu.).

Rf: 0.46 (toluene:AcOEt=8:1); $C_{58}H_{95}O_{10}$ MW: 952.379; $^1$H-NMR (CDCl$_3$) δ: 4.900 (dd, 1H, J=3.4, 10.3 Hz, H-3), 4.882 (d, 1H, J=11.7 Hz, Bn), 4.634 (d, 2H, J=12.2 Hz, 2Bn), 4.543 (d, 1H, J=11.2 Hz, Bn), 4.437 (d, 1H, J=7.3 Hz, H-1), 4.299 (dd, 1H, J=6.8, 11.2 Hz, H-6), 4.087 (dd, 1H, J=6.8, 11.2 Hz, H-6'), 3.850 (d, 1H, J=2.9 Hz, H-4), 3.765 (dd, 1H, J=7.8, 10.3 Hz, H-2), 1.926 (s, 3H, Ac), 1.188 (s, 9H, piv), 0.881 (t, 6H, J=6.8 Hz, 2CH$_3$).

(f) 3,4-di-O-Benzyl-2-deoxy-6-O-levuloyl-2-phtalimido-β-D-gulcopyranosyl-(1→3)-2,4-di-O-benzyl-6-O-pivaloyl-β-D-galactopyranosyl-(1→1)-2,3-di-O-tetradecyl-sn-glycerol (9)

Compound 7 (685 mg, 0.752 mmol), cyclopentadiene hafnonium dichloride (571 mg, 1.96 mmol), silver triflate (771 g, 3.91 mmol) and molecular sieve 4A (2.5 g) were suspended in 1,2-dichloroethane (10 ml). The suspension was stirred at room temperature under argon gas flow, and cooled to −15° C. Compound 2 (563 mg, 0.98 mmol) was added thereto, and the mixture was stirred 1 hour. The reaction mixture was neutralized by addition of triethylamine, diluted with ethyl acetate, and filtered through Celite. The filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=9:1) to obtain Compound 9 (1.01 g, 91.5%)

Rf: 0.44 (toluene:AcOEt=6:1); $C_{89}H_{124}O_{17}N$ MW: 1479.949; $^1$H-NMR (CDCl$_3$) δ: 5.461 (d, 1H, J=8.3 Hz, H-1b), 4.941 (d, 1H, J=11.2 Hz, Bn), 4.874 (d, 1H, J=10.7 Hz, Bn), 4.789 (d, 1H, J=11.7 Hz, Bn), 4.648 (d, 1H, J=11.2 Hz, Bn), 4.536 (d, 1H, J=11.7 Hz, Bn), 4.460 (d, 1H, J=11.7 Hz, Bn), 4.414 (d, 2H, J=11.7 Hz, 2Bn), 4.223 (d, 1H, J=7.8 Hz, H-1a), 3.897 (d, 1H, J=3.2 Hz, H-4a), 2.130 (s, 3H, CH$_3$), 1.153 (s, 9H, piv), 0.881 (t, 6H, J=6.6 Hz, 2CH$_3$).

(g) 2-Acetamido-3,4-di-O-benzyl-2-deoxy-β-D-gulcopyranosyl-(1→3)-2,4-di-O-benzyl-β-D-galactopyranosyl-(1→1)-2,3-di-O-tetradecyl-sn-glycerol (10)

Compound 9 (977.4 mg, 0.667 mmol) was suspended in ethanol (33.5 mL). Hydrazine hydrate (3.35 mL) was added thereto, and the mixture was stirred at 110° C. for 18 hours. The solvent was evaporated, and the obtained amino compound was dissolved in pyridine (6.0 mL). Acetic anhydride (5.0 mL) was added thereto, and the mixture was stirred at the room temperature for 17 hours. Then, the solvent was evaporated. The residue was dissolved in a mixture of methanol and tetrahydrofuran (1:1, 20.0 mL). Sodium methoxide (108 mg, 2.0 mmol) was added thereto, and the mixture was stirred at 60° C. for 1 hour. The reaction mixture was neutralized with Amberlist 15E (H$^+$) type, and filtered through Celite, and the filtrate was evaporated. The residue was purified by silica gel column chromatography (toluene:acetone:CHCl$_3$=5:2:1), and further purified with Sephadex LH-20 (CHCl$_3$:MeOH=2:3) to obtain Compound 10 (756 mg, 94.8%).

Rf: 0.18 (toluene:acetone:CHCl$_3$=6:2:1); C$_{73}$H$_{110}$O$_{13}$N MW: 1209.666; $^1$H-NMR (CDCl$_3$) δ: 4.823 (d, 1H, J=8.3 Hz, H-1b), 4.354 (d, 1H, J=6.8 Hz, H-1a), 1.497 (s, 3H, NHAc), 0.881 (t, 6H, J=6.4 Hz, 2CH$_3$); $^{13}$C-NMR (CDCl$_3$+ CD$_3$OD) δ: 173.06 (Me—$\underline{C}$O), 105.51, 104.01 (C-1×2), 62.80, 62.51 (C-6×2).

(h) 2-Acetamido-3,4-di-O-benzyl-2-deoxy-6-O-sulfo-β-D-gulcopyranosyl-(1→3)-2,4-di-O-benzyl-6-O-sulfo-β-D-galactopyranosyl-(1→1)-2,3-di-O-tetradecyl-sn-glycerol Disodium Salt (11)

Compound 10 (200 mg, 0.165 mmol) was dissolved in N,N-dimethylformamide (1.5 mL). (C$_2$H$_5$)$_3$NSO$_3$ (300 mg, 1.65 mmol) was added thereto, and the mixture was stirred at 50° C. for 0.5 hours. The reaction mixture was directly purified with Sephadex LH-20 (CHCl$_3$:MeOH=2:3). The solvent was evaporated to some extent, and water (2.0 mL) and Dowex-50 (Na$^+$) type were added to the residue, and the mixture was stirred for one day. Then, the mixture was filtered through Celite, and the filtrate was evaporated. The residue was purified with a column of Dowex-50 (Na$^+$) type (CHCl$_3$:MeOH:H$_2$O=5:10:3) to obtain Compound 11 (215 mg, 92.2%).

Rf: 0.38 (CHCl$_3$:MeOH=6:1); C$_{73}$H$_{108}$O$_{19}$NS$_2$Na$_2$ MW: 1413.74; $^1$H-NMR (CDCl$_3$+CD$_3$OD) δ: 4.403 (d, 1H, J=7.8 Hz, H-1a), 1.593 (s, 3H, NHAc), 0.889 (t, 6H, J=6.4 Hz, 2CH$_3$); $^{13}$C-NMR (CDCl$_3$+CD$_3$OD) δ: 172.93 (Me—$\underline{C}$O), 105.24, 104.01 (C-1×2), 68.13, 68.00 (C-6×2).

(i) 2-Acetamido-2-deoxy-6-O-sulfo-β-D-gulcopyranosyl-(1→3)-6-O-sulfo-β-D-galactopyranosyl-(1→1)-2,3-di-O-tetradecyl-sn-glycerol Disodium Salt (12)

Compound 11 (200 mg, 0.141 mmol) was dissolved in a mixture of methanol and water (3:1, 15 mL), and palladium hydroxide/carbon (200 mg) was added thereto. Inside of the reaction system was replaced with hydrogen gas, and catalytic reduction was performed at room temperature for 4 hours. The reaction mixture was filtered through Celite, and the filtrate was evaporated. The residue was purified with a column of Sephadex LH-20 (CHCl$_3$:MeOH:H$_2$O=5:10:3), further purified with a column of Dowex-50 (Na$^+$) type (CHCl$_3$:MeOH:H$_2$O=1:3:1), and finally purified with a column of Sephadex LH-20 (CHCl$_3$:MeOH:H$_2$O=5:10:3) again to obtain Compound 12 (119.6 mg, 80.5%).

Rf: 0.52 (CHCl$_3$:MeOH:H$_2$O=12:8:1); C$_{45}$H$_{84}$O$_{19}$NS$_2$Na$_2$ MW: 1053.24; $^1$H-NMR (DMSO+D$_2$O) δ: 4.666 (d, 1H, J=8.3 Hz, H-1b), 4.162 (d, 1H, J=7.3 Hz, H-1a), 4.067 (b.dd, 1H, H-6b), 4.006–3.924 (b.dd, 1H, H-6a), 1.882 (s, 3H, NHAc), 0.861 (t, 6H, J=6.8 Hz, 2CH$_3$); $^{13}$C-NMR (DMSO+D$_2$O) δ: 171.32 (Me—$\underline{C}$O), 103.49, 102.37 (C-1×2), 65.91, 65.85 (C-6×2).

Example 4

Synthesis of Octyl 2-Acetamido-2-deoxy-6-O-sulfo-β-D-glucopyranosyl-(1→3)-6-O-sulfo-β-D-galactopyranoside Disodium Salt Octyl 2-acetamido-2-deoxy-6-O-sulfo-β-D-glucopyranosyl-(1→3)-6-O-sulfo-β-D-galactopyranoside disodium salt was synthesized according to the scheme outlined in FIG. 6.

The numbers after the substance names represent numbers of compounds in FIG. 6.

(a) Octyl 2,4-di-O-Acetyl-3,6-di-O-allyl-β-D-galactopyranoside (13)

Octanol (300 mg, 2.30 mmol), cyclopentadiene hafnonium dichloride (1.75 g, 5.99 mmol), silver triflate (2.36 g, 12.0 mmol) and molecular sieve 4A (2.3 g) were suspended in 1,2-dichloroethane (5.0 ml), and the suspension was, stirred at room temperature under argon gas flow, and cooled to −15° C. Compound 1 (1.2 g, 3.47 mmol) was added thereto, and the mixture was stirred for 2.5 hours. The reaction mixture was neutralized by addition of triethylamine, diluted with ethyl acetate, and filtered through Celite. The filtrate was washed successively with saturated aqueous sodium hydrogencarbonate and saturated brine. The ethyl acetate layer was dried over magnesium sulfate, and then the solvent was evaporated under reduced pressure. The residue was purified by silica gel column chromatography (toluene:AcOEt=10:1) to obtain Compound 13 (0.8 g, 76%).

Rf: 0.46 (toluene:AcOEt=6:1); 0.34 (hexane:AcOEt=5:1); C$_{24}$H$_{40}$O$_8$ MW: 456.572; $^1$H-NMR (CDCl$_3$) δ: 5.855 (m, 1H, Allyl), 5.784 (m, 1H, Allyl), 5.472 (d, 1H, J=3.4 Hz, H-4), 5.086 (dd, 1H, J=7.8, 9.8 Hz, H-2), 4.394 (d, 1H, J=7.8 Hz, H-1), 2.125, 2.066 (2s, 6H, 2Ac), 0.879 (t, 3H, J=6.8 Hz, CH$_3$).

(b) Octyl 3,6-di-O-Allyl-2,4-di-O-benzyl-β-D-galactopyranoside (15)

Compound 13 (0.8 g, 1.75 mmol) was dissolved in a mixture of methanol and tetrahydrofuran (1:1, 5 mL). 1 N Sodium hydroxide solution (1.0 mL) was added thereto, and the mixture was stirred at room temperature for one day. The reaction mixture was neutralized with Amberlist 15E (H$^+$) type, and filtered through Celite, and the filtrate was evaporated. The residue was purified by silica gel column chromatography (toluene:AcOEt=5:2) to obtain Compound 14 (585 g, 89.7%).

Rf: 0.32 (toluene AcOEt=2:1).

Then, Compound 14 (585 mg, 1.57 mmol) was dissolved in N,N-dimethylformamide (3 ml). Sodium hydride (451 mg, 10.2 mmol) was added thereto, and the mixture was stirred at −15° C. under argon gas flow. Subsequently, benzyl bromide (1.22 ml, 10.2 mmol) was added to the reaction mixture, and it was stirred for 3 hours while the temperature was gradually raised to room temperature. After addition of methanol to the reaction mixture, it was neutralized, diluted with ethyl acetate, and washed successively with saturated aqueous sodium hydrogencarbonate and saturated brine. The ethyl acetate layer was dried over magnesium sulfate, and the solvent was evaporated under reduced pressure. The residue was purified by silica gel column chromatography (hexane:AcOEt=15:1) to obtain Compound 15 (811 mg, 93.5%).

Rf: 0.79 (hexane:AcOEt=6:1); C$_{34}$H$_{48}$O$_6$ MW: 552.747; $^1$H-NMR (CDCl$_3$) δ: 5.947 (m, 1H, Allyl), 5.849 (m, 1H, Allyl), 4.959 (d, 1H, J=11.7 Hz, Bn), 4.915 (d, 1H, J=10.7 Hz, Bn), 4.765 (d, 1H, J=10.7 Hz, Bn), 4.660 (d, 1H, J=11.7 Hz, Bn), 4.346 (d, 1H, J=7.6 Hz, H-1), 0.887 (t, 3H, J=6.4 Hz, CH$_3$).

(c) Octyl 2,4-di-O-Benzyl-β-D-galactopyranoside (16)

Iridium complex (1,5-cyclooctadiene bis (methyldiphenylphosphine)iridium hexafluorophosphate, 172 mg, 0.15 mmol) was suspended in tetrahydrofuran (5 mL), and activated by stirring under H$_2$ flow. Compound 15 (811 mg, 1.47 mmol) dissolved in tetrahydrofuran (5 mL) was added to the solution, and the mixture was stirred at room temperature for 1 hour under argon gas flow. Iodine (745 mg), water (38 mL), and tetrahydrofuran (15 mL) were added thereto, and the mixture was further stirred at room temperature for 1 hour. The reaction mixture was diluted with chloroform, and then washed successively with saturated sodium thiosulfate solution, saturated aqueous sodium hydrogencarbonate, and saturated brine. The chloroform layer was dried over magnesium sulfate, and the solvent was evaporated under reduced pressure. The residue was purified by silica gel column chromatography (toluene:EtOAc=5:2) to obtain Compound 16 (589 mg, 82.1%). Rf: 0.35 (toluene:AcOEt=2:1)

$C_{28}H_{40}O_6$ MW: 472.618 $^1$H-NMR (CDCl$_3$) δ: 5.000 (d, 1H, J=11.7 Hz, Bn), 4.843 (d, 1H, J=11.7 Hz, Bn), 4.674 (d, 1H, J=11.7 Hz, Bn), 4.662 (d, 1H, J=11.7 Hz, Bn), 4.360 (d, 1H, J=7.3 Hz, H-1), 3.776 (d, 1H, J=2.0 Hz, H-4), 0.868 (t, 3H, J=6.8 Hz, CH$_3$)

(d) Octyl 2,4-di-O-Benzyl-6-O-pivaloyl-β-D-galactopyranoside (17)

Compound 16 (569 mg, 1.20 mmol) was dissolved by addition of pyridine (17 mL). Pivaloyl chloride (188 μl, 1.57 mmol) was added to the solution, and the mixture was stirred at −5° C. for 1 hour. Pivaloyl chloride (188 μl, 1.57 mmol) was further added thereto, and the mixture was stirred at −5° C. for 1 hour. The reaction mixture was diluted with ethyl acetate, and filtered through Celite, and the filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 17 (648 mg, 96.7%).

Rf: 0.56 (toluene:AcOEt=6:1); $C_{33}H_{48}O_7$ MW: 556.735; $^1$H-NMR (CDCl$_3$) δ: 4.986 (d, 1H, J=11.2 Hz, Bn), 4.838 (d, 1H, J=11.7 Hz, Bn), 4.664 (d, 1H, J=11.7 Hz, Bn), 4.653 (d, 1H, J=11.7 Hz, Bn), 4.332 (d, 1H, J=7.3 Hz, H-1), 4.316 (dd, 1H, J=6.8, 11.7 Hz, H-6), 4.113 (dd, 1H, J=6.7, 11.0 Hz, H-6'), 3.772 (d, 1H, J=2.4 Hz, H-4), 1.180 (s, 9H, piv), 0.867 (t, 3H, J=6.8 Hz, CH$_3$).

(e) Octyl 3-O-Acetyl-2,4-di-O-benzyl-6-O-pivaloyl-β-D-galactopyranoside (18)

Compound 17 (10 mg, 18.0 μmol) was dissolved by addition of pyridine (1 mL). Acetic anhydride (0.5 mL) was added to the solution, and the mixture was stirred at the room temperature for 2 hours. The solvent was subjected to azeotropy with toluene, and the residue was purified with Sephadex LH-20 (CHCl$_3$:MeOH=1:2) to obtain Compound 18 (11 mg, qu.).

Rf: 0.58 (toluene:AcOEt=8:1); $C_{35}H_{50}O_8$ MW: 598.772; $^1$H-NMR (CDCl$_3$) δ: 4.903 (dd, 1H, J=3.2, 10.0 Hz, H-3), 4.883 (d, 1H, J=11.7 Hz, Bn), 4.645 (d, 1H, J=11.7 Hz, Bn), 4.638 (d, 1H, J=11.7 Hz, Bn), 4.545 (d, 1H, J=11.2 Hz, Bn), 4.405 (d, 1H, J=7.3 Hz, H-1), 4.311 (dd, 1H, J=6.8, 10.8 Hz, H-6), 4.087 (dd, 1H, J=6.8, 10.7 Hz, H-6'), 3.847 (d, 1H, J=2.9 Hz, H-4), 3.769 (dd, 1H, J=7.8, 10.3 Hz, H-2), 1.937 (s, 3H, Ac), 1.188 (s, 9H, piv), 0.870 (t, 3H, J=6.8 Hz, CH$_3$).

(f) Octyl 3,4-di-O-benzyl-2-deoxy-6-O-levuloyl-2-phtalimido-β-D-glucopyranosyl-(1→3)-2,4-di-O-benzyl-6-O-pivaloyl-β-D-galactopyranoside (19)

Compound 17 (624 mg, 1.12 mmol), cyclopentadiene hafnonium dichloride (850 mg, 2.91 mmol), silver triflate (1.15 g, 5.82 mmol) and molecular sieve 4A (3.2 g) were suspended in 1,2-dichloroethane (10 ml), and the suspension was stirred at room temperature under argon gas flow, and cooled to −15° C. Compound 2 (838 mg, 1.46 mmol) was added thereto, and the mixture was stirred for 1 hour. The reaction mixture was neutralized by addition of triethylamine, diluted with ethyl acetate, and filtered through Celite, and the filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 19 (1.03 g, 82.9%).

Rf: 0.47 (toluene:AcOEt=6:1); $C_{66}H_{79}O_{15}N$ MW: 1126.342; $_1$H-NMR (CDCl$_3$) δ: 5.475 (d, 1H, J=8.3 Hz, H-1b), 4.189 (d, 1H, J=7.8 Hz, H-1a), 3.874 (d, 1H, J=2.4 Hz, H-4a), 2.133 (s, 3H, CH$_3$), 1.153 (s, 9H, piv), 0.826 (t, 3H, J=7.1 Hz, CH$_3$).

(g) Octyl 2-Acetamido-3,4-di-O-benzyl-2-deoxy-β-D-glucopyranosyl-(1→3)-2,4-di-O-benzyl-β-D-galactopyranoside (20)

Compounds 19 (1.0 g, 0.899 mmol) was suspended in ethanol (45 mL). Hydrazine hydrate (4.5 mL) was added thereto, and the mixture was stirred at 110° C. for 18 hours. The solvent was evaporated, and the obtained amino compound was dissolved in pyridine (5.0 mL). Acetic anhydride (4.0 mL) was added to the solution, and the mixture was stirred at the room temperature for 17 hour, and the solvent was evaporated. The residue was dissolved in a mixture of methanol and tetrahydrofuran (1:1, 20.0 mL). Sodium methoxide (146 mg, 2.7 mmol) was added thereto, and the mixture was stirred at 60° C. for 1 hour. The reaction mixture was neutralized with Amberlist 15E (H$^+$) type, and filtered through Celite, and the filtrate was evaporated. The residue was purified by silica gel column chromatography (toluene:acetone=2.3:1), and further purified with Sephadex LH-20 (CHCl$_3$:MeOH=2:3) to obtain Compound 20 (739 mg, 96%).

Rf: 0.49 (toluene:acetone=3:2); $C_{50}H65O_{11}N$ MW: 856.06; $^1$H-NMR (CDCl$_3$) δ: 4.840 (d, 1H, J=8.3 Hz, H-1b), 4.329 (d, 1H, J=6.8 Hz, H-1a), 1.515 (s, 3H, NHAc), 0.848 (t, 3H, J=6.8 Hz, CH$_3$); $^{13}$C-NMR (CDCl$_3$+CD$_3$OD) δ: 173.17 (Me—$\underline{C}$O), 105.32, 104.01 (C-1×2), 62.82, 62.55 (C-6×2).

(h) Octyl 2-Acetamido-3,4-di-O-benzyl-2-deoxy-6-O-sulfo-β-D-glucopyranosyl-(1→3)-2,4-di-O-benzyl-6-O-sulfo-β-D-galactopyranoside Disodium Salt (21)

Compound 20 (150 mg, 0.175 mmol) was dissolved in N,N-dimethylformamide (1.5 mL). (C$_2$H$_5$)$_3$NSO$_3$ (319 mg, 1.75 mmol) was added thereto, and the mixture was stirred at 50° C. for 0.5 hours. The reaction mixture was directly purified with Sephadex LH-20 (CHCl$_3$:MeOH=2:3). The solvent of the eluate was evaporated to some extent, and water (2.0 mL) and Dowex-50 (Na$^+$) type were added to the residue, and the mixture was stirred for one day, and filtered through Celite. The filtrate was evaporated, and the residue was purified with a column of Dowex-50 (Na$^+$) type (CHCl$_3$:MeOH:H$_2$O=5:10:3) to obtain Compound 21 (185 mg, 99.6%).

Rf: 0.23 (CHCl$_3$:MeOH=6:1); $C_{50}H_{63}O_{17}NS_2Na_2$ MW: 1060.134; $^1$H-NMR (CDCl$_3$+CD$_3$OD) δ: 4.382 (d, 1H, J=7.3 Hz, H-1a), 1.634 (s, 3H, NHAc), 0.854 (t, 3H, J=6.8 Hz, CH$_3$); $^{13}$C-NMR (CDCl$_3$+CD$_3$OD) δ: 173.03 (Me—$\underline{C}$O), 105.10, 103.99 (C-1×2), 68.18 (C-6×2).

(i) Octyl 2-Acetamido-2-deoxy-6-O-sulfo-β-D-glucopyranosyl-(1→3)-6-O-sulfo-β-D-galactopyranoside Disodium Salt (22)

Compound 21 (170 mg, 0.160 mmol) was dissolved in a mixture of methanol and water (3:1, 15 mL) and palladium hydroxide/carbon (180 mg) was added thereto. Inside of the reaction system was replaced with hydrogen gas, and catalytic reduction was performed at room temperature for 4 hours. The reaction mixture was filtered through Celite, and the filtrate was evaporated. The residue was purified with a column of Sephadex LH-20 (CHCl$_3$:MeOH:H$_2$O=5:10:3), further purified with a column of Dowex-50 (Na$^+$) type (CHCl$_3$:MeOH:H$_2$O=1:3:1), and finally purified with a column of Sephadex LH-20 (CHCl$_3$:MeOH:H$_2$O=5:10:3) again to obtain Compound 22 (101.4 mg, 90.6%).

Rf: 0.30 (CHCl$_3$:MeOH:H$_2$O=12:6:1); C$_{22}$H$_{39}$O$_{17}$NS$_2$Na$_2$ MW: 699.636; $^1$H-NMR (DMSO+D$_2$O): δ: 4.655 (d, 1H, J=8.3 Hz, H-1b), 4.136 (d, 1H, J=7.8 Hz, H-1a), 4.053 (dd, 1H, J=2.0, 11.7 Hz, H-6b), 3.956–3.851 (b.dd, 1H, H-6a), 1.869 (s, 3H, NHAc), 0.861 (t, 3H, J=7.1 Hz, CH$_3$); $^{13}$C-NMR (DMSO+D$_2$O) δ: 171.19 (Me—$\underline{C}$O), 102.98, 102.30 (C-1×2), 66.09, 65.87 (C-6×2).

Example 5
Syntheses of Cholestanyl 2-Acetamido-2-deoxy-6-O-sulfo-β-D-glucopyranosyl-(1→3)-6-O-sulfo-β-D-galactopyranoside Disodium Salt and Cholestanyl 2-Acetamido-2-deoxy-β-D-glucopyranosyl-(1→3)-β-D-galactopyranoside According to the scheme outlined in FIG. 7, cholestanyl 2-acetamido-2-deoxy-6-O-sulfo-β-D-glucopyranosyl-(1→3)-6-O-sulfo-β-D-galactopyranoside disodium salt and cholestanyl 2-acetamido-2-deoxy-β-D-glucopyranosyl-(1→3)-β-D-galactopyranoside were synthesized.

The numbers after the substance names represent numbers of compounds in FIG. 7.

(a) Cholestanyl 2,4-di-O-Acetyl-3,6-di-O-allyl-β-D-galactopyranoside (23)

Cholestanol (700 mg, 1.80 mmol), cyclopentadiene hafnonium dichloride (1.37 g, 4.68 mmol), silver triflate (1.85 g, 9.37 mmol) and molecular sieve 4A (2.7 g) were suspended in 1,2-dichloroethane (7.0 ml), and the suspension was stirred at room temperature under argon gas flow, and cooled to −10° C. Compound 1 (936 mg, 2.70 mmol) was added thereto, and the mixture was stirred for 2.5 hours. The reaction mixture was neutralized by addition of triethylamine, diluted with ethyl acetate, and filtered through Celite, and the filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 23 (970 mg, 75.3%).

Rf: 0.57 (toluene:AcOEt=6:1); C$_{43}$H$_{70}$O$_8$ MW: 715.018; $^1$H-NMR (CDCl$_3$) δ: 5.880 (m, 1H, Allyl), 5.802 (m, 1H, Allyl), 5.480 (d, 1H, J=3.4 Hz, H-4), 5.072 (dd, 1H, J=8.3, 10.3 Hz, H-2), 4.510 (d, 1H, J=8.3 Hz, H-1), 2.150, 2.095 (2s, 6H, 2Ac), 0.922 (d, 3H, J=6.4 Hz, CH$_3$), 0.890 (d, 3H, J=6.8 Hz, CH$_3$), 0.885 (d, 3H, J=6.4 Hz, CH$_3$), 0.800, 0.667 (2s, 6H, 2CH$_3$).

(b) Cholestanyl 3,6-di-O-allyl-2,4-di-O-benzyl-β-D-galactopyranoside (25)

Compound 23 (0.98 g, 1.37 mmol) was dissolved in a mixture of methanol and tetrahydrofuran (1:1, 10 mL). 1 N Sodium hydroxide solution (1.0 mL) was added thereto, and the mixture was stirred at room temperature for one day. Sodium methoxide (74 mg, 1.37 mmol) was further added thereto, and the mixture was stirred at room temperature for 2 hours. The reaction mixture was neutralized with Amberlist 15E (H$^+$) type, and filtered through Celite, and the filtrate was evaporated. The residue was purified by silica gel column chromatography (toluene:AcOEt=5:2) to obtain Compound 24 (0.83 g, 96%).

Rf: 0.33 (toluene:AcOEt=2:1).

Then, Compound 24 (838 mg, 1.32 mmol) was dissolved in N,N-dimethylformamide (8 ml). Sodium hydride (378 mg, 8.58 mmol) was added thereto, and the mixture was stirred at 0° C. under argon gas flow. Then, benzyl bromide (1.02 ml, 8.58 mmol) was added to the reaction mixture, and it was stirred for 3 hours while the temperature was gradually raised to room temperature. Sodium hydride (378 mg, 8.58 mmol) and benzyl bromide (1.02 ml, 8.58 mmol) were further added to the reaction mixture, and it was stirred for 18 hours. After addition of methanol to the reaction, it was neutralized, diluted with ethyl acetate, and washed successively with saturated aqueous sodium hydrogencarbonate and saturated brine. The ethyl acetate layer was dried over magnesium sulfate, and the solvent was evaporated under reduced pressure. The residue was purified by silica gel column chromatography (hexane:AcOEt=13:1) to obtain Compound 25 (0.94 g, 88.1%).

Rf: 0.72 (hexane:AcOEt=6:1); C$_{53}$H$_{78}$O$_6$ MW: 811.193; $^1$H-NMR (CDCl$_3$) δ: 5.935 (m, 1H, Allyl), 5.836 (m, 1H, Allyl), 4.931 (d, 1H, J=11.7 Hz, Bn), 4.903 (d, 1H, J=10.7 Hz, Bn), 4.739 (d, 1H, J=10.7 Hz, Bn), 4.639 (d, 1H, J=11.7 Hz, Bn), 4.438 (d, 1H, J=7.8 Hz, H-1), 3.829 (d, 1H, J=2.9 Hz, H-4), 3.719 (dd, 1H, J=7.8, 9.8 Hz, H-2), 3.397 (dd, 1H, J=2.9, 9.8 Hz, H-3), 0.893 (d, 3H, J=6.4 Hz, CH$_3$), 0.862 (d, 3H, J=6.8 Hz, CH$_3$), 0.858 (d, 3H, J=6.4 Hz, CH$_3$), 0.799, 0.641 (2s, 6H, 2CH$_3$).

(c) Cholestanyl 2,4-di-O-Benzyl-β-D-galactopyranoside (26)

Iridium complex (1,5-cyclooctadiene bis (methyldiphenylphosphine)iridium hexafluorophosphate, 136 mg, 0.12 mmol) was suspended in tetrahydrofuran (5 mL), and activated by stirring under H$_2$ flow. To this solution Compound 25 (940 mg, 1.16 mmol) dissolved in tetrahydrofuran (5 mL) was added, and the mixture was stirred at room temperature for 1 hour under argon gas flow. Iodine (588 mg), water (30 mL) and tetrahydrofuran (15 mL) were added thereto, and the mixture was further stirred at room temperature for 1.5 hours. The reaction mixture was diluted with chloroform, and washed successively with saturated sodium thiosulfate solution, saturated aqueous sodium hydrogencarbonate, and saturated brine. The chloroform layer was dried over magnesium sulfate, and the solvent was evaporated under reduced pressure. The residue was purified by silica gel column chromatography (toluene:acetone=6:1) to obtain Compound 26 (748 mg, 88.2%).

Rf: 0.49 (toluene:acetone=4:1); C$_{47}$H$_{70}$O$_6$ MW: 731.064; $^1$H-NMR (CDCl$_3$) δ: 5.006 (d, 1H, J=11.2 Hz, Bn), 4.823 (d, 1H, J=11.2 Hz, Bn), 4.678 (d, 1H, J=10.7 Hz, Bn), 4.650 (d, 1H, J=11.7 Hz, Bn), 4.476 (d, 1H, J=6.8 Hz, H-1).

(d) Cholestanyl 2,4-di-O-Benzyl-6-O-pivaloyl-β-D-galactopyranoside (27)

Compound 26 (647 mg, 0.885 mmol) was dissolved in pyridine (13 mL). To the solution, pivaloyl chloride (138 μl, 1.15 mmol) was added, and the mixture was stirred at −5 to 0° C. for 0.5 hour. Pivaloyl chloride (138 μl, 1.15 mmol) was further added thereto, and the mixture was stirred at −5 to 0° C. for 1 hour. The reaction mixture was diluted with ethyl acetate, and filtered through Celite, and the filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 27 (663 mg, 91.9%).

Rf: 0.56 (toluene:AcOEt=6:1); C$_{52}$H$_{78}$O$_7$ MW: 815.181; $^1$H-NMR (CDCl$_3$) δ: 4.993 (d, 1H, J=11.7 Hz, Bn), 4.821 (d, 1H, J=11.2 Hz, Bn), 4.667 (d, 1H, J=11.2 Hz, Bn), 4.642 (d, 1H, J=11.7 Hz, Bn), 4.450 (d, 1H, J=7.3 Hz, H-1), 4.293 (dd, 1H, J=6.8, 11.2 Hz, H-6), 4.083 (dd, 1H, J=6.3, 10.8 Hz, H-6'), 3.746 (d, 1H, J=2.0 Hz, H-4), 1.176 (s, 9H, piv).

(e) Cholestanyl 3-O-Acetyl-2,4-di-O-benzyl-6-O-pivaloyl-β-D-galactopyranoside (28)

Compound 27 (10 mg, 12.3 μmol) was dissolved in pyridine (1 mL). To the solution, acetic anhydride (0.5 mL) was added, and the mixture was stirred at the room temperature for 1 hour. The solvent was subjected to azeotropy with toluene, and the residue was purified with Sephadex LH-20 (CHCl$_3$:MeOH=1:2) to obtain Compound 28 (9 mg, 85.4%).

Rf: 0.65 (toluene:AcOEt=8:1); $C_{54}H_{80}O_8$ MW: 857.218; $^1$H-NMR (CDCl$_3$) δ: 4.889 (dd, 1H, J=2.7, 10.5 Hz, H-3), 4.885 (d, 1H, J=11.2 Hz, Bn), 4.647 (d, 1H, J=11.7 Hz, Bn), 4.625 (d, 1H, J=11.2 Hz, Bn), 4.533 (d, 1H, J=11.7 Hz, Bn), 4.518 (d, 1H, J=7.3 Hz, H-1), 4.289 (dd, 1H, J=6.8, 11.2 Hz, H-6), 4.061 (dd, 1H, J=6.3, 11.2 Hz, H-6'), 3.766 (d, 1H, J=2.4 Hz, H-4), 3.753 (dd, 1H, J=7.3, 10.3 Hz, H-2), 1.924 (s, 3H, Ac), 1.185 (s, 9H, piv)

(f) Cholestanyl 3,4-di-O-Benzyl-2-deoxy-6-O-levuloyl-2-phtalimido-β-D-glucopyranosyl-(1→3)-2,4-di-O-benzyl-6-O-pivaloyl-β-D-galactopyranoside (29)

Compound 27 (737 mg, 0.904 mmol), cyclopentadiene hafnonium dichloride (686 mg, 2.35 mmol), silver triflate (927 mg, 4.70 mmol), and molecular sieve 4A (2.5 g) were suspended in 1,2-dichloroethane (10 ml), the suspension was stirred at room temperature under argon gas flow, and cooled to −15° C. Compound 2 (676.5 mg, 1.18 mmol) was added thereto, and the mixture was stirred for 1 hour. The reaction mixture was neutralized by addition of triethylamine, diluted with ethyl acetate, and filtered through Celite, and the filtrate was washed successively with saturated aqueous sodium hydrogencarbonate and saturated brine. The ethyl acetate layer was dried over magnesium sulfate, and the solvent was evaporated under reduced pressure. The residue was purified by silica gel column chromatography (toluene:AcOEt=10:1) to obtain Compound 29 (982.1 mg, 79.3%).

Rf: 0.58 (toluene:AcOEt=6:1); 0.07 (hexane:AcOEt=6:1); $C_{85}H_{109}O_{15}N$ MW: 1384.788; $^1$H-NMR (CDCl$_3$) δ: 5.475 (d, 1H, J=8.3 Hz, H-1b), 4.453 (d, 1H, J=7.8 Hz, H-1a), 3.852 (d, 1H, J=2.9 Hz, H-4a), 2.133 (s, 3H, CH$_3$), 1.146 (s, 9H, piv)

(g) Cholestanyl 2-Acetamido-3,4-di-O-benzyl-2-deoxy-β-D-glucopyranosyl-(1→3)-2,4-di-O-benzyl-β-D-galactopyranoside (30)

Compound 29 (668 mg, 0.488 mmol) was suspended in ethanol (24.5 mL). Hydrazine hydrate (2.45 mL) was added thereto, and the mixture was stirred at 110° C. for 18 hours. The solvent was evaporated, and the obtained amino compound was dissolved in pyridine (5.0 mL). To the solution, acetic anhydride (4.0 mL) was added, and the mixture was stirred at the room temperature for 17 hour, and the solvent was evaporated. The residue was dissolved in a mixture of methanol and tetrahydrofuran (1:1, 10.0 mL). Sodium methoxide (78.8 mg, 1.46 mmol) was added thereto, and the mixture was stirred 60° C. for 1 hour. The reaction mixture was neutralized with Amberlist 15E (H$^+$) type, and filtered through Celite, and the filtrate was evaporated. The residue was purified by silica gel column chromatography (toluene:acetone=3:1), and further purified with Sephadex LH-20 (CHCl$_3$:MeOH=2:3) to obtain Compound 30 (534.2 mg, 99.6%).

Rf: 0.34 (toluene:acetone=3:1); $C_{69}H_{95}O_{11}N$ MW: 1114.506; $^1$H-NMR (CDCl$_3$) δ: 5.044 (d, 1H, J=12.2 Hz, NH), 4.875 (d, 1H, J=11.2 Hz, Bn), 4.851 (d, 1H, J=7.8 Hz, H-1b), 4.809 (d, 1H, J=11.2 Hz, Bn), 4.740 (d, 1H, J=11.7 Hz, Bn), 4.696 (d, 1H, J=11.7 Hz, Bn), 4.672 (d, 1H, J=12.2 Hz, Bn), 4.642 (d, 1H, J=10.7 Hz, Bn), 4.571 (d, 1H, J=12.2 Hz, Bn), 4.562 (d, 1H, J=12.2 Hz, Bn), 4.439 (d, 1H, J=6.4 Hz, H-1a), 1.524 (s, 3H, NHAc), 0.892 (d, 3H, J=6.3 Hz, CH$_3$), 0.860 (d, 3H, J=6.8 Hz, CH$_3$), 0.856 (d, 3H, J=6.8 Hz, CH$_3$), 0.760, 0.635 (2s, 6H, 2CH$_3$); $^{13}$C-NMR (CDCl$_3$+CD$_3$OD) δ: 173.00 (Me—$\underline{C}$O), 103.79, 103.06 (C-1×2), 62.77, 62.40 (C-6×2)

(h) Cholestanyl 2-Acetamido-3,4-di-O-benzyl-2-deoxy-6-O-sulfo-β-D-glucopyranosyl-(1→3)-2,4-di-O-benzyl-6-O-sulfo-β-D-galactopyranoside Disodium Salt (31)

Compound 30 (150 mg, 0.136 mmol) was dissolved in N,N-dimethylformamide (1.5 mL). (C$_2$H$_5$)$_3$NSO$_3$ (247 mg, 1.36 mmol) was added thereto, and the mixture was stirred at 50° C. for 0.5 hour. The reaction mixture was directly purified with Sephadex LH-20 (CHCl$_3$:MeOH=2:3). The solvent of the eluate was evaporated to some extent, and water (2.0 mL) and Dowex-50 (Na$^+$) type were added to the residue, and the mixture was stirred for one day, and filtered through Celite. The filtrate was evaporated, and the residue was purified with a column of Dowex-50 (Na$^+$) type (CHCl$_3$:MeOH:H$_2$O=5:10:3) to obtain Compound 31 (175 mg, 97.3%).

Rf: 0.22 (CHCl$_3$:MeOH=8:1); $C_{69}H_{93}O_{17}NS_2Na_2$ MW: 1318.58; $^1$H-NMR (CD$_3$OD) δ: 4.523 (d, 1H, J=7.3 Hz, H-1a), 4.384 (dd, 1H, J=2.0, 10.8 Hz, H-6b), 4.290 (dd, 1H, J=4.4, 10.7 Hz, H-6a), 1.645 (s, 3H, NHAc), 0.910 (d, 3H, J=6.8 Hz, CH$_3$), 0.873 (d, 3H, J=6.4 Hz, CH$_3$), 0.868 (d, 3H, J=6.8 Hz, CH$_3$), 0.730, 0.658 (2s, 6H, 2CH$_3$); $^{13}$C-NMR (CDCl$_3$+CD$_3$OD) δ: 102.97, 102.55 (C-1×2), 68.47, 67.22 (C-6×2).

(i) Cholestanyl 2-Acetamido-2-deoxy-6-O-sulfo-β-D-glucopyranosyl-(1→43)-6-O-sulfo-β-D-galactopyranoside Disodium Salt (32)

Compound 31 (170 mg, 0.129 mmol) was dissolved in a mixture of methanol and water (3:1, 15 mL), and palladium hydroxide/carbon (180 mg) was added thereto. Inside of the reaction system was replaced with hydrogen gas, and catalytic reduction was performed at room temperature for 4 hours. The reaction mixture was filtered through Celite, and the residue was evaporated. The residue was purified with a column of Sephadex LH-20 (CHCl$_3$:MeOH:H$_2$O=5:10:3), further purified with a column of Dowex-50 (Na$^+$) type (CHCl$_3$:MeOH:H$_2$O=1:3:1), and finally purified with a column of Sephadex LH-20 (CHCl$_3$:MeOH:H$_2$O=5:10:3) again to obtain Compound 32 (109.4 mg, 88.6%).

Rf: 0.47 (CHCl$_3$:MeOH:H$_2$O=12:8:1); $C_{41}H_{69}O_{17}NS_2Na_2$ MW: 958.08; $^1$H-NMR (CDCl$_3$) δ: 4.727 (d, 1H, J=7.8 Hz, H-1b), 4.310 (d, 1H, J=7.8 Hz, H-1a), 4.093 (b.dd, 1H, H-6b), 4.010–3.924 (b.dd, 1H, H-6a), 1.926 (s, 3H, NHAc), 0.945 (d, 3H, J=6.4 Hz, CH$_3$), 0.909 (d, 3H, J=6.4 Hz, CH$_3$), 0.905 (d, 3H, J=6.8 Hz, CH$_3$), 0.827, 0.689 (2s, 6H, 2CH$_3$); $^{13}$C-NMR (DMSO+D$_2$O) δ: 170.88 (Me—$\underline{C}$O), 102.21, 100.73 (C-1×2), 65.85, 65.65 (C-6×2)

(j) Cholestanyl 2-Acetamido-2-deoxy-β-D-glucopyranosyl-(1→3)-β-D-galactopyranoside (33)

Compound 30 (230 mg, 0.209 mmol) was dissolved in a mixture of methanol, water and ethyl acetate (4:1:1, 25 mL), and palladium hydroxide/carbon (230 mg) was added thereto. Inside of the reaction system was replaced with hydrogen gas, and catalytic reduction was performed at room temperature for 20 hours. The reaction mixture was filtered through Celite, and the filtrate was evaporated. The residue was purified with a column of Sephadex LH-20 (CHCl$_3$:MeOH=1:1) to obtain Compound 33 (126.1 mg, 81.5%).

Rf: 0.51 (CHCl$_3$:MeOH=3:1); $C_{41}H_{71}O_{11}N$ MW: 754.008; $^1$H-NMR (C$_5$D$_5$N+D$_2$O) δ: 5.383 (d, 1H, J=8.3 Hz, H-1b), 4.825 (d, 1H, J=7.3 Hz, H-1a), 2.059 (s, 3H, NHAc).

Example 6

Tests for Safety and Pharmacological Efficacy

Figure 8:
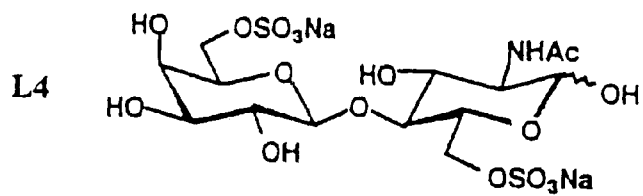
FIG. 8 shows structures of keratan sulfate oligosaccharides.
Figure 8:
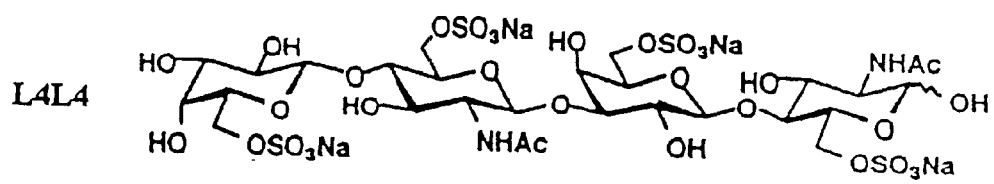
Figure 8:
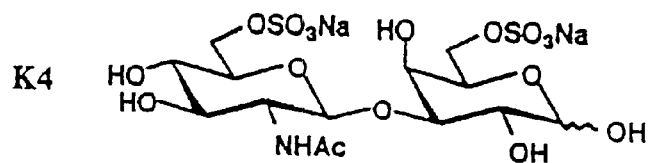
Figure 8:
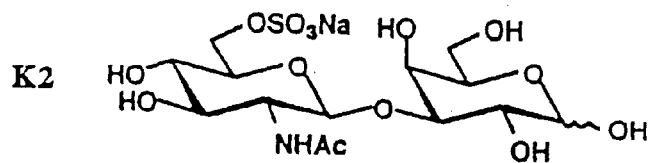
Figure 8:
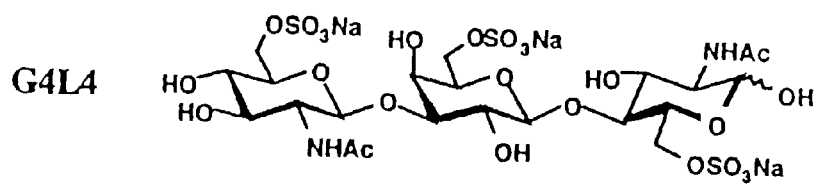

In this example, sodium salt of L4, sodium salt of keratan sulfate tetrasaccharide (L4L4) which consists of two L4 linked through β1-3 linkage, sodium salt of K4 (Compound 28 in Example 1), sodium salt of K2, and sodium salt of G4L4 (see FIG. 8 as for the structures of the oligosaccharides represented by these abbreviations) were used as the keratan sulfate oligosaccharide. L4 and L4L4 were obtained by the method described in International Publication WO96/16973.

The sodium salt of K2 was obtained as follows.

10 g of keratan sulfate derived from bovine cornea was dissolved in 120 ml of 0.1 M Tris/HCl buffer (pH 7.5). The keratan sulfate was decomposed by adding 1000 units of keratanase derived from Pseudomonas sp. (produced by Seikagaku Corporation) to the solution and incubating the solution at 37° C. for 50 hours. After the reaction was completed, and 1.3-fold volume of ethanol was added to the solution, and the mixture was stirred, and left at room temperature overnight. On the next day, the solution was separated into supernatant and precipitate by centrifugation (10,000 rpm, 20 minutes), and the supernatant was concentrated under reduced pressure. The concentrate was lyophilized to obtain 9 g of dried material. The obtained dried material was dissolved in a small amount of distilled water, subjected to gel chromatography utilizing Cellulofine GCL-90m (produced by CHISSO Corporation, 4.5 cm×125 cm) and 0.2 M sodium chloride solution as an eluent to obtain a fraction containing K2. The obtained K2 fraction was concentrated under reduced pressure, desalted by gel filtration chromatography utilizing Cellulofine GCL-25m (produced by CHISSO Corporation, 4.0 cm×120 cm) and distilled water as eluent, and lyophilized.

This lyophilized fraction containing K2 was dissolved in a small amount of distilled water, loaded on Muromac 1×4 (200–400) (produced by Muromachi Kagaku Co., Ltd., 2.0 cm×32 cm), and eluted with a linear gradient of 0 to 2 M sodium chloride to separate a further purified K2 fraction. The obtained K2 fraction was concentrated under reduced pressure, desalted by gel filtration chromatography utilizing Cellulofine GCL-25m (produced by CHISSO Corporation, 4.0 cm×120 cm), and lyophilized to obtain 1.9 g of dried K2.

(1) Test for Safety
1. Toxicity Test by Single Administration in Mice

K4 or G4L4 was intravenously administered once to normal mice (each group consists of 5 mice) at a dose of 2,000 mg/kg, and the mice were observed for the general condition for 14 days.

No death was observed for both of the male and female groups. While paralytic gait was observed for every mouse immediately after the administration of K4 or G4L4, all mice restored normal condition within about 3 minutes after the administration. As for body weight, while male mice showed slight weight loss on the next day of the administration, all mice showed favorable body weight increase thereafter. In autopsies, no abnormality due to the K4 or G4L4 administration was observed for all mice. From the above results, the least fatal dose of K4 and G4L4 for single intravenous administration is considered to be 2,000 mg/kg or higher. Therefore, $LD_{50}$ of K4 and G4L4 for single intravenous administration exceeds 2,000 mg/kg for both of male and female mice.

2. Test for Antigenicity in Guinea Pigs

Guinea pigs were sensitized by 3 times of subcutaneous administration of K4 or G4L4 alone or an emulsion of K4 with an immunostimulant, Freund's complete adjuvant (FCA). K4 or G4L4 was intravenously administered to the animals 12 days after the final sensitization to induce active systemic anaphylaxis. As a positive control, a similar test was performed for ovalbumin (OVA).

The results of the above test were shown in Table 1 together with the doses of the test substances. No anaphylatic reaction was observed in the K4- or G4L4-induced guinea pigs. The positive control in the test, ovalbumin-induced guinea pig, showed anaphylatic reaction. From the above results, K4 and G4L4 are not considered to induce active systemic anaphylaxis in guinea pigs.

TABLE 1

Antigenicity test of K4 and G4L4

| Test substance | N | Sensitization | | Induction | | Evaluation |
|---|---|---|---|---|---|---|
| | | Dose (mg/animal/administration) | Administration route | Dose (mg/animal/administration) | Administration route | |
| K4 | 5 | 0.4 | s.c. | 10 | i.v. | − |
| G4L4 | 5 | 0.4 | s.c. | 10 | i.v. | − |
| K4 + FCA | 5 | 4.0 | s.c. | 10 | i.v. | − |
| OVA | 3 | 1.0 | s.c. | 3 | i.v. | + |

In Table 1, s.c. means subcutaneous injection, and i.v. means intravenous injection.

(2) Test for Pharmacological Efficacy
1. Investigation of Effect on Increase of Blood Vessel Permeability Induced by Calcium-ionophore Under ether anesthesia, rats were shaved on their back, and 0.1 ml of a solution of calcium-ionophore (A23187, Wako Pure Chemicals Industries, 10 μg/ml) dissolved in 2% DMSO was intracutaneously administered to each rat at one site. As a negative control, 0.1 ml of 2% DMSO solution was intracutaneously administered at one site. Each test substance was dissolved in the calcium-ionophore solution, and 0.1 ml of the solution was intracutaneously administered at several sites. Immediately after that, 1 ml of Evans Blue was intravenously administered to each rat, and each rat was killed by exsanguination 30 minutes later. The skin was exfoliated, and the Evans Blue leaking site was punched with a trephine. The punched piece was used for the measurement of the amount of the leaked dye. The amount of the leaked dye was measured according to the method of Katayama et al. (Microbiol. Immunol., 22, 89–101 (1978)). That is, the obtained skin was hydrolyzed with 1 N KOH overnight, neutralized with a 0.6 N $H_3PO_4$ solution in acetone (mixed at a ratio of 5:13), and then centrifuged. The amount of the leaked dye was determined based on the absorbance (620 nm) of the supernatant.

Figure 9:
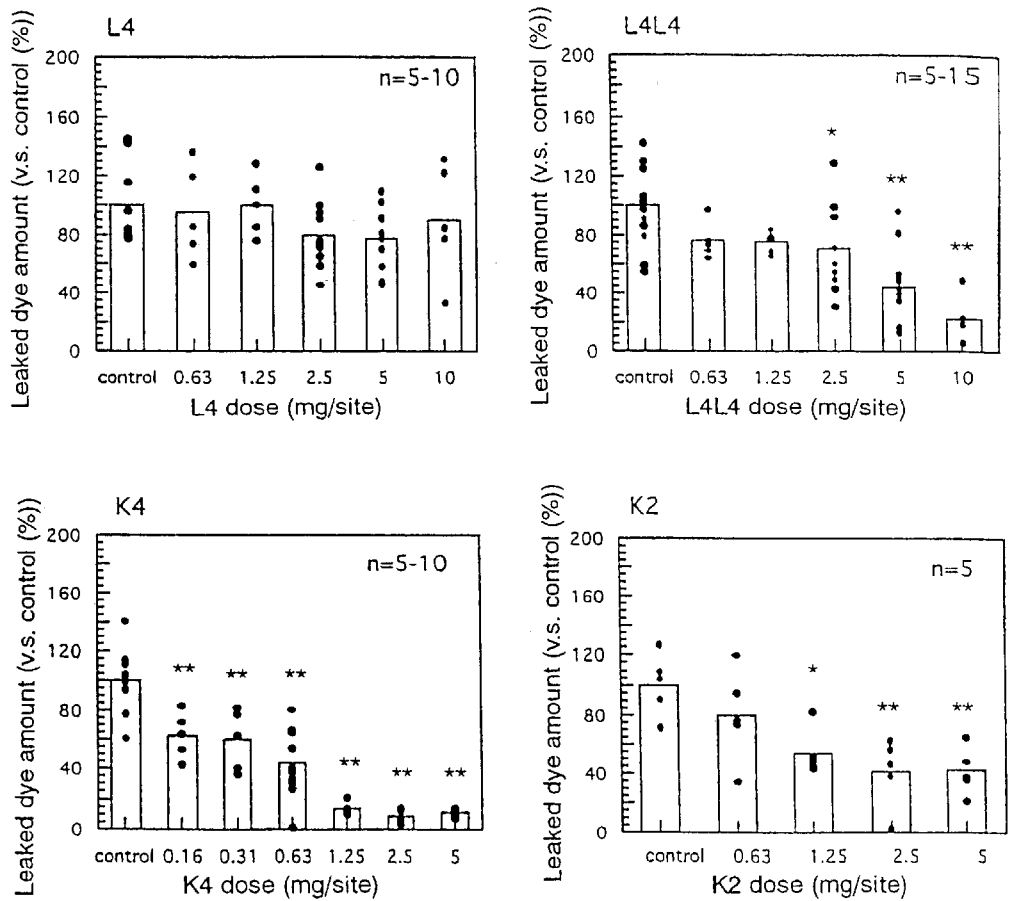
FIG. 9 shows effect of a keratan sulfate oligosaccharide on increase of blood vessel permeability.
Figure 10:
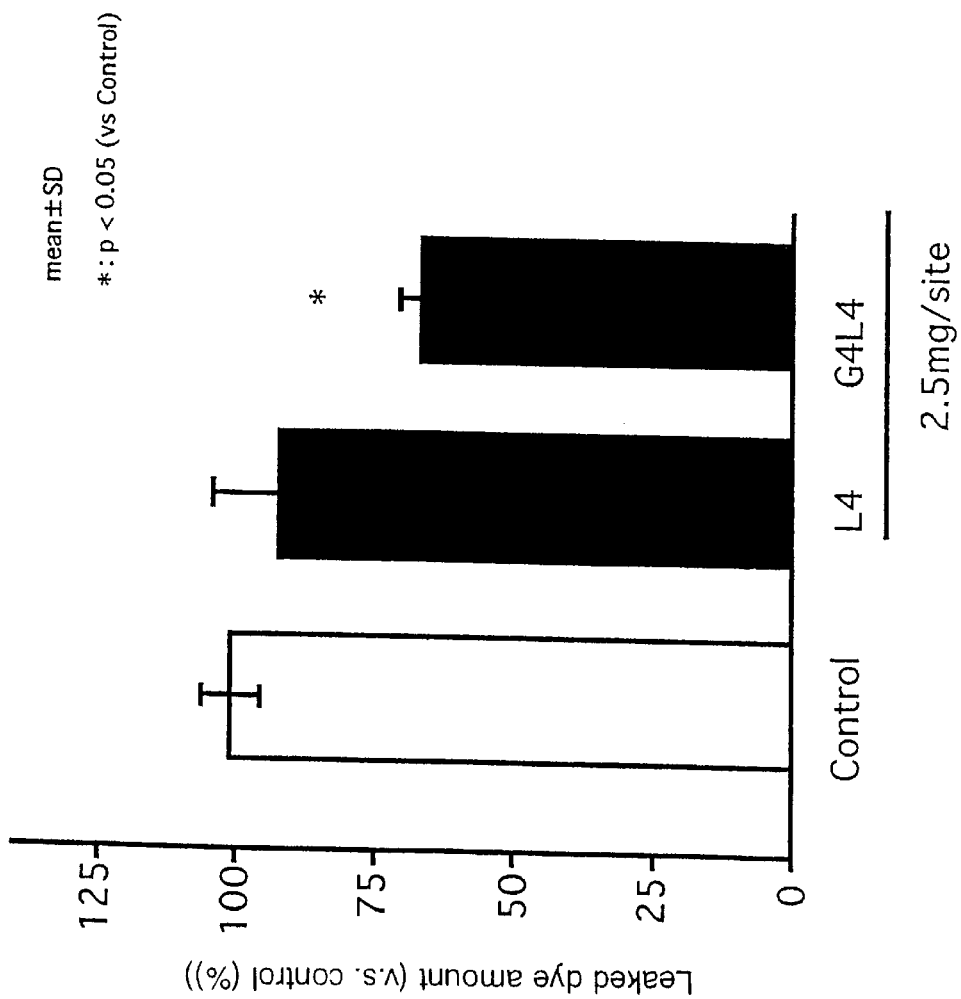
FIG. 10 shows effect of a keratan sulfate oligosaccharide on increase of to blood vessel permeability.

The results obtained by using L4, L4L4, K4 and K2 as test substances are shown in FIG. 9. The results obtained by using L4 and G4L4 as test substances are shown in FIG. 10.

L4L4, K4 and K2 dose-dependently suppressed the increase of blood vessel permeability, and they showed significant suppression effect at concentrations of 2.5 to 10 mg/site, 0.63 to 5 mg/site and 1.25 to 5 mg/site, respectively. The strongest suppression effect was shown by K4; K2 showed weaker effect; and L4L4 showed further weaker effect. G4L4 also showed significant suppression effect against increase of blood vessel permeability. On the other hand, L4 hardly suppressed increase of blood vessel permeability in this model. These results suggest that K4, K2, L4L4 and G4L4 may show anti-allergy activity by suppressing increase of blood vessel permeability. In particular, it is suggested that excellent activity may be shown by K4.

Because L4L4, K4, K2 and G4L4 significantly suppressed increase of blood vessel permeability induced by calcium-ionophore in this test, it was suggested that K2 structure is important for expression of the activity, and the activity was enhanced by the K4 structure. Moreover, since L4 did not show the suppression activity, it was suggested that the L4 structure was not so important in this model. On the other hand, L4L4, which consists of two L4 structures linked through β-(1–3) linkage, was presumed to show the suppression activity in this model, since it had the K4 structure. It was suggested that L4L4, K4, K2 and G4L4 suppressed the increase of blood vessel permeability by stabilizing membranes to inhibit inflow of $Ca^{2+}$ into cells or inhibiting degranulation, or suppressing histamine and so forth secreted from mast cells.

2. Investigation of Effect on $O_2^-$ Generation by Guinea Pig Neutrophils Induced by FMLP (N-Formyl-Met-Leu-Phe) Stimulation A 0.2% aqueous solution of glycogen in physiological saline was autoclaved, and 20 ml of the solution was intraperitoneally administered to a Hartley female guinea pig. The animal was killed by exsanguination 16 hours later, 20 ml of physiological saline containing 10 U/ml of heparin was injected into the abdominal cavity, and the peritoneal exudate was collected. The exudate was centrifuged at 1000 rpm for 10 minutes on a desk-top centrifugal machine, and purified water was added to the precipitate to cause hemolysis for 30 seconds. The solution was made isotonic again with Hank's balanced salt solution at 2-fold concentration, and centrifuged at 1000 rpm for 10 minutes. A procedure of resuspension of the precipitates in the Hank's balanced salt solution and centrifugation was repeated twice to obtain neutrophils. The obtained guinea pig neutrophils were suspended in Hank's balanced salt solution, and the leukocyte number was counted by a blood cell counter (Sysmex K-2000). A suspension diluted with Hank's balanced salt solution to $2 \times 10^6$ cells/ml was used for the experiment as a cell suspension.

1 ml of the-cell suspension and 10 μl of a solution of test substance at a known concentration (in a control, keratan sulfate oligosaccharide was not added) were mixed, preincubated at 37° C. for 1 hour, and 50 μl of 1.6 mM cytochrome C solution and 100 μl of 0.1 mM FMLP solution were successively added thereto and mixed. The mixture was incubated at 37° C. for 10 minutes, and the reaction was stopped by cooling with ice. The reaction mixture was centrifuged at 3000 rpm for 5 minutes, and absorbance of the supernatant was measured at a wavelength of 550 nm. All of the aforementioned procedures except for the incubation were performed with ice cooling.

Figure 11:
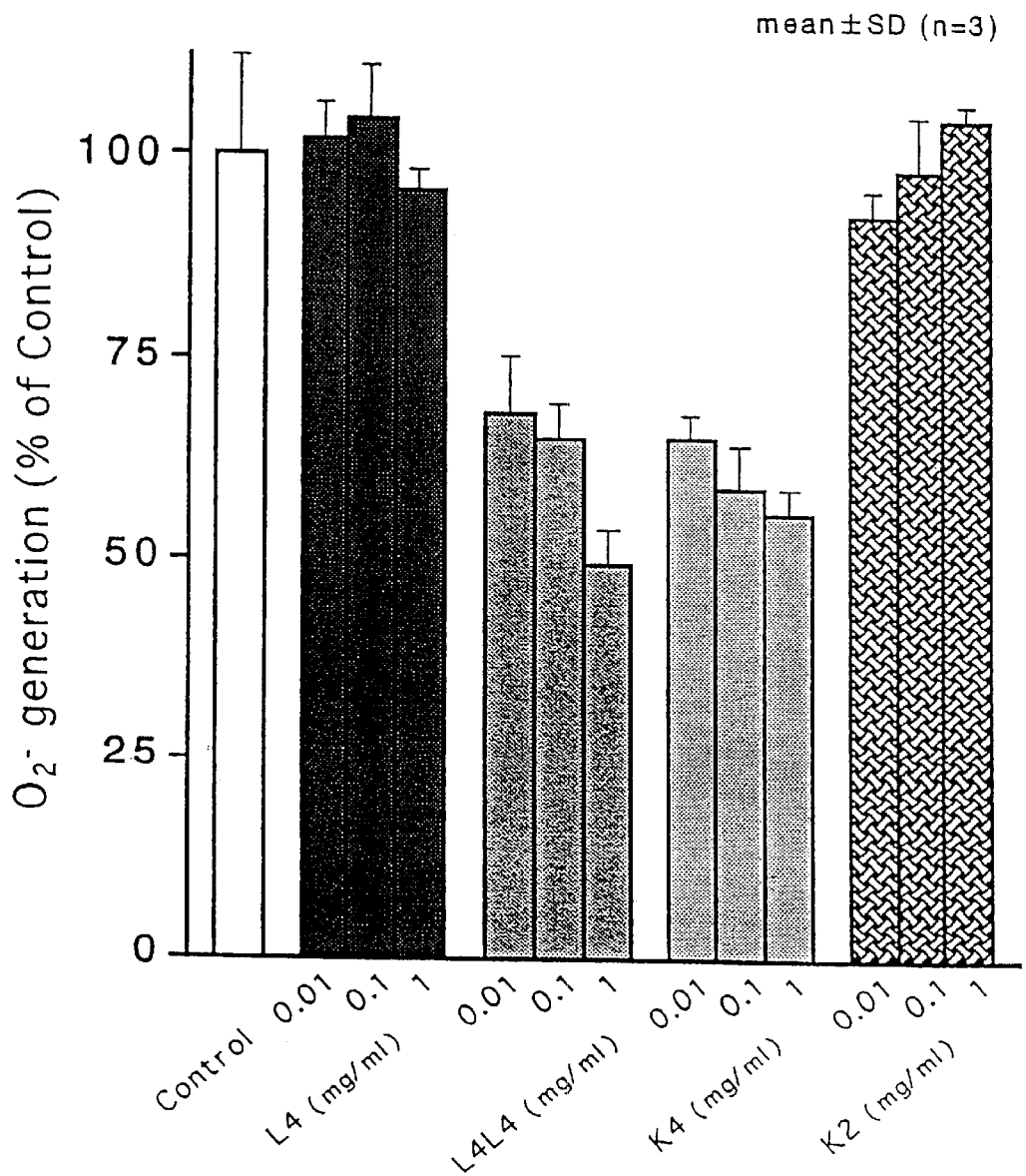
FIG. 11 shows effect of a keratan sulfate oligosaccharide on $O_2^-$ generation by neutrophils.
Figure 12:
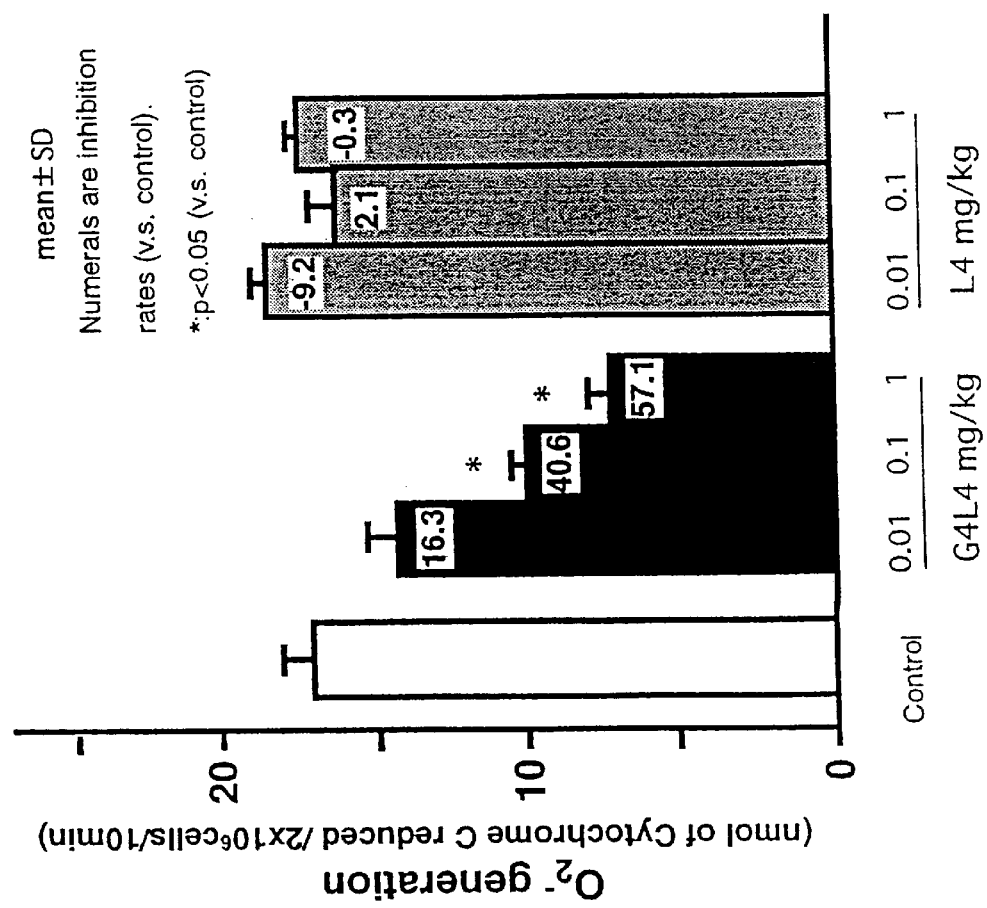
FIG. 12 shows effect of a keratan sulfate oligosaccharide on $O_2^-$ generation by neutrophils.

The results obtained by using L4, L4L4, K4 and K2 as test substances are shown in FIG. 11. The results obtained by using L4 and G4L4 as test substances are shown in FIG. 12.

L4L4, K4 and G4L4 markedly suppressed the $O_2^-$ generation by neutrophils induced by FMLP stimulation at a concentration of 0.01 to 1 mg/ml. They showed relative inhibition rates to the control of 50.6%, 44.7% and 57.1%, respectively, at a concentration of 1 mg/ml. L4 and K2 showed substantially no $O_2^-$ generation suppression effect. These results suggest that L4L4, K4 and G4L4 show anti-inflammatory activity by suppressing the generation of active oxygen by neutrophils.

In this test, K4 showed the suppression effect, but L4 did not, in spite of the fact that L4 and K4 had the same charge, empirical formula, and constituent saccharides. Further, L4L4 showed suppression effect, but K4, which was a constituent saccharide of L4K4, did not show the effect. The fact that L4L4, K4 and G4L4 significantly suppressed $O_2^-$ generation by guinea pig neutrophils induced by FMLP stimulation suggested that the K4 structure was important for expression of the activity. Moreover, since K2 did not show the suppression effect, it was suggested that the degree of the sulfation was important in this model. It was also suggested that L4L4, K4 and G4L4 having the K4 structure may express the activity by inhibiting the stimulus transmission system including GTP binding protein and phospholipase C, or directly competing with respect to the FMLP receptors.

What is claimed is:

1. An oligosaccharide represented by the following general formula (13):

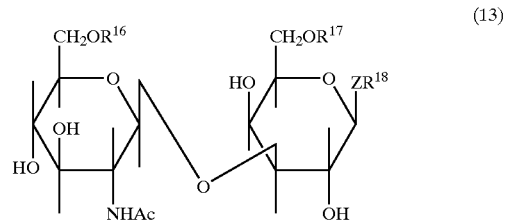

wherein $R^{16}$ and $R^{17}$ each represent —$SO_3M$ where M represents a proton or a monovalent cation, Ac represents an acetyl group, $R^{18}$ represents a hydrogen atom, an alkyl group, a glycerol residue, an O-alkylglycerol residue, an O-acylglycerol residue, a cholesterol residue, a cholestanyl group, a ceramide residue, a phospholipid residue, a biotin residue, or a peptide residue, and Z represents an oxygen atom or —NHCO—.

2. The oligosaccharide according to claim 1, wherein Z is an oxygen atom.

3. The oligosaccharide according to claim 1, wherein Z is an oxygen atom and $R^{18}$ is a hydrogen atom.

4. The oligosaccharide according to claim 1, wherein Z is an oxygen atom and $R^{18}$ is an alkyl group.

5. The oligosaccharide according to claim 1, wherein Z is an oxygen atom and $R^{18}$ is an O-alkylglycerol residue.

6. The oligosaccharide according to claim 1, wherein Z is an oxygen atom and $R^{18}$ is a cholestanyl group.

* * * * *